United States Patent
Wang et al.

(10) Patent No.: US 11,041,849 B2
(45) Date of Patent: Jun. 22, 2021

(54) METHODS AND SYSTEMS FOR IDENTIFYING CANDIDATE NUCLEIC ACID AGENT

(71) Applicant: APTITUDE MEDICAL SYSTEMS, INC., Santa Barbara, CA (US)

(72) Inventors: Jinpeng Wang, Santa Barbara, CA (US); Brian Ferguson, Santa Barbara, CA (US); Qiang Gong, Santa Barbara, CA (US)

(73) Assignee: APTITUDE MEDICAL SYSTEMS, INC., Goleta, CA (US)

(*) Notice: Subject to any disclaimer, the term of this patent is extended or adjusted under 35 U.S.C. 154(b) by 57 days.

(21) Appl. No.: 16/463,671

(22) PCT Filed: Nov. 14, 2017

(86) PCT No.: PCT/US2017/061439
§ 371 (c)(1),
(2) Date: May 23, 2019

(87) PCT Pub. No.: WO2018/102115
PCT Pub. Date: Jun. 7, 2018

(65) Prior Publication Data
US 2019/0324022 A1   Oct. 24, 2019

Related U.S. Application Data
(60) Provisional application No. 62/428,958, filed on Dec. 1, 2016.

(51) Int. Cl.
| | | |
|---|---|---|
| A61K 48/00 | (2006.01) |
| C07H 21/04 | (2006.01) |
| G01N 33/53 | (2006.01) |
| C12N 15/10 | (2006.01) |
| C12N 15/115 | (2010.01) |
| C40B 30/04 | (2006.01) |
| C40B 40/06 | (2006.01) |
| G01N 33/566 | (2006.01) |

(52) U.S. Cl.
CPC ..... *G01N 33/5308* (2013.01); *C12N 15/1048* (2013.01); *C12N 15/115* (2013.01); *C40B 30/04* (2013.01); *C40B 40/06* (2013.01); *G01N 33/566* (2013.01); *C12N 2320/11* (2013.01)

(58) Field of Classification Search
CPC .......... C12N 2310/16; C12N 15/115
See application file for complete search history.

(56) References Cited

U.S. PATENT DOCUMENTS
| | | | |
|---|---|---|---|
| 5,582,981 A | 12/1996 | Toole et al. | |
| 2015/0376620 A1* | 12/2015 | Ikebukuro | C12N 15/115 435/6.1 |

FOREIGN PATENT DOCUMENTS
| | | |
|---|---|---|
| WO | 2007084886 A2 | 7/2007 |
| WO | 2012152711 A1 | 11/2012 |
| WO | 2014088830 A2 | 6/2014 |

OTHER PUBLICATIONS

Wang et al. "Particle display: a quantitative screening method for generating high-affinity aptamers," Angew Chem Int Ed Engl, Mar. 18, 2014 (Mar. 18, 2014), vol. 53, No. 19, pp. 4796-4801. entire document.
Wang et al. "Multiparameter Particle Display (MPPD): A Quantitative Screening Method for the Discovery of Highly Specific Aptamers," Angew Chem Int Ed Engl, Dec. 9, 2016 (Dec. 9, 2016), vol. 56, No. 3, pp. 744-747. entire document.
Raddatz MSL et. al. "Enrichment of Cell-Targeting and Population-Specific Aptamers by Fluorescence-Activated Cell Sorting", Angewandte Chemie International Edition, vol. 47, No. 28, Jun. 27, 2008 (Jun. 27, 2008) p. 5190-5193.
Mayer G. et. al. "Fluorescence-activated cell sorting for aptamer SELEX with cell mixtures" Nature Protocols, vol. 5, No. 12, Dec. 1, 2010 (Dec. 1, 2010), p. 1993-2004.
EPO communication pursuant to Art 94(3) EPC in EP178761912 dated Feb. 10, 2021.

* cited by examiner

*Primary Examiner* — Amy H Bowman
(74) *Attorney, Agent, or Firm* — IPro, PLLC

(57) ABSTRACT

The present disclosure provides methods, kits and compositions for identifying nucleic acid agents having a desired property, e.g., a property of specifically binding to a target (such as a protein target) with high affinity. More specifically, the present disclosure provides methods, kits and compositions for identifying candidate nucleic acid agents with both high specificity and affinity for a target.

12 Claims, 7 Drawing Sheets
Specification includes a Sequence Listing.

METHODS AND SYSTEMS FOR IDENTIFYING CANDIDATE NUCLEIC ACID AGENT

STATEMENT REGARDING FEDERALLY SPONSORED RESEARCH

This invention was made with government support under Grant No. 1R44GM109721 awarded by National Institute of General Medical Sciences (NIGMS). The government has certain rights in the invention.

BACKGROUND

Since their initial description, aptamers have shown considerable promise as a synthetic alternative to monoclonal antibodies. They possess numerous important advantages, including thermostability, ease of chemical synthesis and modification, and the capacity for reversible folding, all of which are valuable characteristics for diverse applications in molecular diagnostics and therapeutics. Unfortunately, the standard aptamer generation process (i.e., Systematic Evolution of Ligands by Exponential Enrichment (SELEX)) often fails to yield aptamers with comparable affinity and specificity relative to antibodies. In addition, obtaining aptamers that simultaneously possess both high affinity and specificity, on a routine basis, has been difficult using conventional aptamer discovery methodologies such as SELEX. Among many reasons, one main challenge is due to the fact that conventional selection can only be performed either for affinity (i.e., positive selection) or for specificity (i.e., negative selection), but not both simultaneously.

SUMMARY

The present disclosure provides methods, kits and compositions for identifying nucleic acid agents having a desired property, e.g., a property of specifically binding to a target (such as a protein target) with high affinity. More specifically, the present disclosure provides methods, kits and compositions for identifying aptamers with both high specificity and affinity for a target.

In one aspect, the present disclosure provides a method for identifying one or more nucleic acid agents having a desired property from a mixture of candidate nucleic acid agents. The mixture of candidate nucleic acid agents may comprise a plurality of single stranded nucleic acids.

The method may comprise providing a plurality of particles with the candidate nucleic acid agents immobilized thereon, wherein each of the plurality of particles may comprise at most a subset of the candidate nucleic acid agents within the mixture. The method may further comprise exposing the plurality of particles to a screening composition comprising a target moiety and a reference moiety, wherein an interaction of the candidate nucleic acid agents with the target moiety may be indicated by a first signal, an interaction of the candidate nucleic acid agents with the reference moiety may be indicated by a second signal, and an intensity of the first signal together with an intensity of the second signal for a particular particle may provide a sorting parameter of the particular particle. A concentration of the target moiety and a concentration of the reference moiety may be respectively set at a value enabling the sorting parameter of about 0.05% to about 1% of the plurality of particles to be within a predetermined sorting range.

The method may further comprise isolating from the plurality of particles one or more selected particles having a sorting parameter within the predetermined sorting range, wherein the one or more selected particles may comprise the one or more nucleic acid agents having the desired property.

The method may further comprise identifying the one or more nucleic acid agents having the desired property from the one or more selected particles.

The method may further comprise immobilizing the mixture of candidate nucleic acid agents onto the plurality of particles.

In some embodiments, the sorting range is determined by a first threshold and a second threshold, and the sorting parameter of a particular particle is within the sorting range when the intensity of the first signal of the particular particle is above the first threshold and the intensity of the second signal of the particular particle is below the second threshold.

In some embodiments, the first threshold is determined by a process comprising exposing the plurality of particles with the mixture of candidate nucleic acid agents immobilized thereon to a first prescreening composition comprising a saturating concentration of the target moiety, and determining a maximum mean intensity of a signal indicating an interaction of the candidate nucleic acid agents with the target moiety in the first prescreening composition, wherein the first prescreening composition does not comprise the reference moiety.

In some embodiments, the first threshold is set to be at least one half of the maximum mean intensity of the signal indicating an interaction of the candidate nucleic acid agents with the target moiety in the first prescreening composition.

In some embodiments, the second threshold is determined by a process comprising exposing the plurality of particles with the mixture of candidate nucleic acid agents immobilized thereon to a second prescreening composition comprising a saturating concentration of the reference moiety, and determining a maximum mean intensity of a signal indicating an interaction of the candidate nucleic acid agents with the reference moiety in the second prescreening composition, wherein the second prescreening composition does not comprise the target moiety.

In some embodiments, the second threshold is set to be at most one tenth of the maximum mean intensity of the signal indicating an interaction of the candidate nucleic acid agents with the reference moiety in the second prescreening composition.

In some embodiments, a ratio between the concentration of the target moiety and the concentration of the reference moiety in the screening composition is from about $1:10^9$ to about 1:1.

In some embodiments, the concentration of the target moiety in the screening composition is from about 0.001 nM to about 1 μM.

In particular, the concentration of the reference moiety in the screening composition is from about 1 nM to about 1 mM.

In some embodiments, each of the plurality of particles comprises multiple copies of a single candidate nucleic acid agent immobilized thereon, and wherein the candidate nucleic acid agent immobilized on any one particle of the plurality of particles is different from that immobilized on at least one other particle of the plurality of particles.

In some embodiments, the target moiety is labeled with a first labeling moiety, and the reference moiety is labeled with a second labeling moiety different from the first labeling moiety. The interaction of the candidate nucleic acid agents with the target moiety may be a binding interaction, which may be indicated by a signal generated from the first labeling moiety of the target moiety. The interaction of the candidate nucleic acid agents with the reference moiety may be a binding interaction, which may be indicated by a signal generated from the second labeling moiety of the reference moiety. In particular, the first labeling moiety and the second labeling moiety may be independently selected from the following agents or an antibody comprising one or more of the following agents: a radioactive isotope, a fluorescer, a chemiluminescer, a chromophore, an enzyme, an enzyme substrate, an enzyme cofactor, an enzyme inhibitor, a dye, a metal ion, a metal sol, a ligand, and an affinity tag.

In some embodiments, the first labeling moiety and the second labeling moiety are independently chosen from the following agents or an antibody comprising any of the following agents: a biotin, an avidin, a streptavidin and a hapten.

In some embodiments, the first labeling moiety and the second labeling moiety are independently chosen from the following agents or an antibody comprising any of the following agents: an acridine dye, a cyanine dye, a fluorone dye, an oxazine dye, a phenanthridine dye, and a rhodamine dye.

For example, the first labeling moiety and the second labeling moiety may be independently selected from the following agents or an antibody comprising one or more of the following agents: AlexaFluor350, AlexaFluor488, AlexaFluor647, AlexaFluor405, AlexaFluor430, AlexaFluor500, AlexaFluor514, AlexaFluor532, AlexaFluor546, AlexaFluor555, AlexaFluor568, AlexaFluor594, AlexaFluor610, AlexaFluor633, AlexaFluor635, AlexaFluor660, AlexaFluor680, AlexaFluor700, AlexaFluor750, and AlexaFluor790.

In some embodiments, the target moiety is a protein or a polypeptide moiety.

In some embodiments, the reference moiety is a protein or a polypeptide moiety.

In particular, the reference moiety may comprise serum proteins.

In some embodiments, the single stranded nucleic acid agent is selected from a DNA molecule, a RNA molecule, a chemically modified DNA molecule, and a chemically modified RNA molecule. In particular, the single stranded nucleic acid agent may be a DNA molecule. In some embodiments, the single stranded nucleic acid agent comprises one or more non-natural nucleic acid. In some embodiments, the single stranded nucleic acid agent is an aptamer.

In some embodiments, one or more of the single stranded nucleic acid agents comprises a molecule conjugated thereto. For example, the molecule conjugated to one or more of the single stranded nucleic acids is a small molecule, a fluorophore, a peptide, and/or an siRNA.

In some embodiments, the desired property is an ability to specifically bind to a target or an activity induced by such specific binding.

For example, the activity induced by such specific binding may be a catalytic activity, a modified catalytic activity, an inhibition activity, an activation activity, a modification of an inhibition activity, an activation activity, a structure switching activity, a modification of a structure switching activity, and/or a cooperative activity.

In some embodiments, the particle is non-magnetic, magnetic or paramagnetic. For example, each of the plurality of particles may have at least one dimension of from about 50 nm to about 100 µm. In some embodiments, the plurality of particles comprises carboxylic acid paramagnetic particles having an average diameter of about 1 µm.

In some embodiments, the plurality of particles comprises from about $1 \times 10^2$ to about $1 \times 10^{14}$ particles.

In some embodiments, each particle of the plurality of particles comprises from about $1 \times 10^2$ to about $1 \times 10^{10}$ candidate nucleic acid agents bound thereto.

In some embodiments, each of the candidate nucleic acid agents is coupled to a particle of the plurality of particles via a linker. The linker may be a cleavable linker, a non-cleavable linker or a combination thereof. In some embodiments, the linker is an amino-modified nucleic acid primer.

In some embodiments, the isolating from the plurality of particles one or more selected particles comprises sorting the plurality of particles using flow cytometry, fluorescence microscopy, an optical tweezer, a micro-pipette, and/or microfluidic magnetic separation. For example, the flow cytometry may be fluorescence activated cell sorting (FACS) or Ramen flow cytometry.

In some embodiments, the first signal and the second signal are fluorescent signal, and wherein the first threshold and the second threshold are fluorescence intensity threshold level.

In some embodiments, the method further comprises, prior to immobilizing the mixture of candidate nucleic acid agents onto a plurality of particles, pre-enriching the candidate nucleic acid agents to obtain a pre-enriched pool of candidate nucleic acid agents to be immobilized on to the plurality of particles, wherein the pre-enriched pool has decreased sequence diversity relative to the mixture of candidate nucleic acid agents prior to pre-enriching.

For example, the pre-enriching may comprise incubating the mixture of candidate nucleic acid agents with a pre-enriching composition comprising the target moiety to facilitate interactions between the candidate nucleic acid agents and the target moiety, and identifying candidate nucleic acid agents capable of interacting with the target moiety. For example, the target moiety in the pre-enriching composition may be immobilized on a bead.

The method may further comprise preparing the mixture of candidate nucleic acid agents by a method comprising generating a library of single stranded nucleic acids, wherein each single stranded nucleic acid in the library may comprise a region of randomized sequence.

The method may further comprise generating an enriched mixture of candidate nucleic acid agents from the selected particle prior to identifying the one or more nucleic acid agents having the desired property from the one or more selected particles.

In some embodiments, the following operations constitute one round of screening: immobilizing the mixture of candidate nucleic acid agents onto a plurality of particles, wherein each of the plurality of particles comprises at most a subset of the candidate nucleic acid agents; exposing the plurality of particles to a screening composition comprising a target moiety and a reference moiety, wherein an interaction of the candidate nucleic acid agents with the target moiety is indicated by a first signal, an interaction of the candidate nucleic acid agents with the reference moiety is indicated by a second signal, and an intensity of the first signal together with an intensity of the second signal for a particular particle provide a sorting parameter of the particular particle, wherein a concentration of the target moiety and a concentration of the reference moiety are respectively set at a value enabling the sorting parameter of about 0.05% to about 1% of the plurality of particles to be within a predetermined sorting range; isolating from the plurality of particles one or more selected particles having a sorting parameter within the predetermined sorting range, wherein the one or more selected particles comprises the one or more nucleic acid agents having the desired property; and generating an enriched mixture of candidate nucleic acid agents from the selected particle. The method may comprise two or more rounds of screening, wherein the enriched mixture of candidate nucleic acid agents obtained from the selected particle of one round of screening may be used as the mixture of candidate nucleic acid agents to be immobilized onto the plurality of particles the next round of screening.

In some embodiments, the one or more nucleic acid agents identified as having a desired property binds to the target moiety with a $K_{DT}$ of from about 1 fM to about 1 μM. In some embodiments, the one or more nucleic acid agents identified as having a desired property binds to the target moiety with a $K_{DT}$ and binds to the reference moiety with a $K_{DR}$, and a ratio between the $K_{DR}$ and the $K_{DT}$ may be from about $10^2$ to $10^{12}$.

In some embodiments, the one or more nucleic acid agents identified as having a desired property binds to the target moiety with a first apparent $K_{DT}$ when the binding occurs in a composition comprising the target moiety but not the reference moiety, and the one or more nucleic acid agents identified as having the desired property binds to the target moiety with a second apparent $K_{DT}$ when the binding occurs in a composition comprising both the target moiety and the reference moiety, and wherein a difference between the first apparent $K_{DT}$ and the second apparent $K_{DT}$ may be less than about 20% of the value of the first apparent $K_{DT}$.

In some embodiments, the enriched mixture of candidate nucleic acid agents is generated by a method comprising nucleic acid amplification. For example, the nucleic acid amplification may comprise PCR or reverse transcriptase PCR.

In some embodiments, when immobilizing the mixture of candidate nucleic acid agents onto the plurality of particles, the mixture of candidate nucleic acid agents may be immobilized onto the plurality of particles by a method comprising emulsion PCR.

In some embodiments, the target moiety comprises a protein or a part thereof selected from the group consisting of Tumor Necrosis Factor α, Neutrophil Gelatinase-Associated Lipocalin, Histidine-Rich Protein 2, Platelet-Derived Growth Factors, Vascular Endothelial Growth Factors, Angiopoietins, Complement proteins and Integrins.

In some embodiments, the reference moiety comprises one or more molecules homologous to the target moiety. For example, the one or more molecules of the reference moiety may have a homology from about 50% to about 99% to the target moiety.

In some embodiments, the reference moiety comprises a mixture comprising proteins, glycans and/or small molecules. For example, the reference moiety may comprise a mixture comprising blood, plasma, serum, liquid humor, vitreous, urine, tissue fluid, spit, and/or saliva.

For example, the blood, plasma, serum, liquid humor, vitreous, urine, tissue fluid, spit, and/or saliva may be from a human being.

In another aspect, the present disclosure provides a nucleic acid agent specifically binding to Tumor Necrosis Factor α or a part thereof. The nucleic acid agent may comprise a sequence as set forth in SEQ ID NO: 1.

In another aspect, the present disclosure provides a nucleic acid agent specifically binding to Neutrophil Gelatinase-Associated Lipocalin or a part thereof. The nucleic acid agent may comprise a sequence as set forth in SEQ ID NO: 3.

In another aspect, the present disclosure provides a nucleic acid agent specifically binding to Histidine-Rich Protein 2or a part thereof. The nucleic acid agent may comprise a sequence as set forth in SEQ ID NO: 4.

In another aspect, the present disclosure provides a kit for identifying one or more nucleic acid agents having a desired property from a mixture of candidate nucleic acid agents. The mixture of candidate nucleic acid agents may comprise a plurality of single stranded nucleic acids. The kit may comprise: a plurality of particles; a mixture of candidate nucleic acid agents to be immobilized onto the plurality of particles; and a screening composition for screening the plurality of particles with the mixture of candidate nucleic acid agents immobilized thereon. In some cases, the kit may comprise, in addition or alternatively, a plurality of particles with the candidate nucleic acid agents immobilized thereon and the screening composition, wherein each of the plurality of particles may comprise at most a subset of the candidate nucleic acid agents within the mixture.

The screening composition may comprise a target moiety and a reference moiety, a concentration of the target moiety and a concentration of the reference moiety in the screening composition may be adjustable to enable sorting out of selected particles with the one or more nucleic acid agents having the desired property immobilized thereon. A percentage of the selected particles may be about 0.05% to about 1% of the plurality of particles screened.

In some embodiments, the screening comprises exposing the plurality of particles with the mixture of candidate nucleic acid agents immobilized thereon to the screening composition. An interaction of the candidate nucleic acid agents with the target moiety may be indicated by a first signal, an interaction of the candidate nucleic acid agents with the reference moiety may be indicated by a second signal, and an intensity of the first signal together with an intensity of the second signal for a particular particle may provide a sorting parameter of the particular particle. The concentration of the target moiety and the concentration of the reference moiety may enable the sorting parameter of about 0.05% to about 1% of the plurality of particles screened to be within a predetermined sorting range.

In some embodiments, the kit further comprises a component for isolating the selected particles.

In some embodiments, the kit further comprises a component for identifying the one or more nucleic acid agents having the desired property from the selected particles.

In some embodiments, the sorting range is determined with a first threshold and a second threshold, and the sorting parameter of a particular particle may be within the sorting range when the intensity of the first signal of the particular particle is above the first threshold and the intensity of the second signal of the particular particle is below the second threshold.

In some embodiments, the kit further comprises a first prescreening composition comprising a saturating concentration of the target moiety while not comprising the reference moiety. The first threshold may be determined by a process comprising: exposing the plurality of particles with the mixture of candidate nucleic acid agents immobilized thereon to the first prescreening composition, and determining a maximum mean intensity of a signal indicating an interaction of the candidate nucleic acid agents with the target moiety in the first prescreening composition.

For example, the first threshold may be set to be at least one half of the maximum mean intensity of the signal indicating an interaction of the candidate nucleic acid agents with the target moiety in the first prescreening composition.

In some embodiments, the kit further comprises a second prescreening composition comprising a saturating concentration of the reference moiety while not comprising the target moiety, wherein the second threshold is determined by a process comprising exposing the plurality of particles with the mixture of candidate nucleic acid agents immobilized thereon to the second prescreening composition, and determining a maximum mean intensity of a signal indicating an interaction of the candidate nucleic acid agents with the reference moiety in the second prescreening composition.

In some embodiments, the second threshold is set to be at most one tenth of the maximum mean intensity of the signal indicating an interaction of the candidate nucleic acid agents with the reference moiety in the second prescreening composition.

In some embodiments, a ratio between the concentration of the target moiety and the concentration of the reference moiety in the screening composition is from about $1:10^9$ to about 1:1.

In some embodiments, the concentration of the target moiety in the screening composition is from about 0.001 nM to about 1 μM.

In some embodiments, the concentration of the reference moiety in the screening composition is from about 1 nM to about 1 mM.

In some embodiments, after immobilizing the mixture of candidate nucleic acid agents onto the plurality of particles, each of the plurality of particles comprises multiple copies of a single candidate nucleic acid agent immobilized thereon. The candidate nucleic acid agent immobilized on any one particle of the plurality of particles may be different from that immobilized on at least one other particle of the plurality of particles.

In some embodiments, the target moiety is labeled with a first labeling moiety, and the reference moiety is labeled with a second labeling moiety different from the first labeling moiety. For example, the interaction of the candidate nucleic acid agents with the target moiety may be a binding interaction, which may be indicated by a signal generated from the first labeling moiety of the target moiety. The interaction of the candidate nucleic acid agents with the reference moiety may be a binding interaction, which may be indicated by a signal generated from the second labeling moiety of the reference moiety.

In some embodiments, the first labeling moiety and the second labeling moiety are independently selected from the following agents or an antibody comprising one or more of the following agents: a radioactive isotope, a fluorescer, a chemiluminescer, a chromophore, an enzyme, an enzyme substrate, an enzyme cofactor, an enzyme inhibitor, a dye, a metal ion, a metal sol, a ligand, and an affinity tag. For example, the first labeling moiety and the second labeling moiety may be independently chosen from the following agents or an antibody comprising any of the following agents: a biotin, an avidin, a streptavidin and a hapten. In some embodiments, the first labeling moiety and the second labeling moiety may be independently chosen from the following agents or an antibody comprising any of the following agents: an acridine dye, a cyanine dye, a fluorone dye, an oxazine dye, a phenanthridine dye, and a rhodamine dye.

For example, the first labeling moiety and the second labeling moiety may be independently selected from the following agents or an antibody comprising one or more of the following agents: AlexaFluor350, AlexaFluor488, AlexaFluor647, AlexaFluor405, AlexaFluor430, AlexaFluor500, AlexaFluor514, AlexaFluor532, AlexaFluor546, AlexaFluor555, AlexaFluor568, AlexaFluor594, AlexaFluor610, AlexaFluor633, AlexaFluor635, AlexaFluor660, AlexaFluor680, AlexaFluor700, AlexaFluor750, and AlexaFluor790.

In some embodiments, the target moiety is a protein or a polypeptide moiety.

In some embodiments, the reference moiety is a protein or a polypeptide moiety.

For example, the reference moiety may comprise serum proteins.

In some embodiments, the single stranded nucleic acid agent is selected from a DNA molecule, a RNA molecule, a chemically modified DNA molecule, and a chemically modified RNA molecule. For example, the single stranded nucleic acid agent may be a DNA molecule. In some embodiments, the single stranded nucleic acid agent comprises one or more non-natural nucleic acid. In some embodiments, the single stranded nucleic acid agent is an aptamer.

In some embodiments, one or more of the single stranded nucleic acid agents comprises a molecule conjugated thereto. For example, the molecule conjugated to one or more of the single stranded nucleic acids may be a small molecule, a fluorophore, a peptide, and/or an siRNA.

In some embodiments, the desired property is an ability to specifically bind to a target or an activity induced by such specific binding. For example, the activity induced by such specific binding may be a catalytic activity, a modified catalytic activity, an inhibition activity, an activation activity, a modification of an inhibition activity, an activation activity, a structure switching activity, a modification of a structure switching activity, and/or a cooperative activity.

In some embodiments, the particle is non-magnetic, magnetic or paramagnetic. In some embodiments, each of the plurality of particles has at least one dimension of from about 50 nm to about 100 μm. For example, the plurality of particles may comprise carboxylic acid paramagnetic particles having an average diameter of about 1 μm.

In some embodiments, the plurality of particles comprises from about $1\times10^2$ to about $1\times10^{14}$ particles. In some embodiments, after immobilizing the mixture of the candidate nucleic acid agents onto the plurality of particles, each particle of the plurality of particles comprises from about $1\times10^2$ to about $1\times10^{10}$ candidate nucleic acid agents bound thereto.

In some embodiments, each of the candidate nucleic acid agents is coupled to a particle of the plurality of particles via a linker. For example, the linker may be a cleavable linker, a non-cleavable linker or a combination thereof. In some embodiments, the linker is an amino-modified nucleic acid primer.

In some embodiments, isolating the selected particles comprises using flow cytometry, fluorescence microscopy, an optical tweezer, a micro-pipette, and/or microfluidic magnetic separation. For example, the flow cytometry may be fluorescence activated cell sorting (FACS) or Ramen flow cytometry. In some embodiments, the first signal and the second signal are fluorescent signal, and the first threshold and the second threshold are fluorescence intensity threshold level.

In some embodiments, the kit further comprises a pre-enriching composition for pre-enriching the candidate nucleic acid agents prior to immobilizing them onto the plurality of particles. The pre-enriching composition may comprise the target moiety, and upon incubating the mixture of candidate nucleic acid agents with the pre-enriching composition, a pre-enriched pool of candidate nucleic acid agents may be obtained to be immobilized onto the plurality of particles. The pre-enriched pool may have decreased sequence diversity relative to the mixture of candidate nucleic acid agents prior to pre-enriching. For example, the target moiety in the pre-enriching composition may be immobilized on a bead.

In some embodiments, the kit further comprises a component for generating an enriched mixture of candidate nucleic acid agents from the selected particle.

In some embodiments, the one or more nucleic acid agents identified as having a desired property binds to the target moiety with a $K_{DT}$ of from about 1 fM to about 1 µM.

In some embodiments, the one or more nucleic acid agents identified as having a desired property binds to the target moiety with a $K_{DT}$ and binds to the reference moiety with a $K_{DR}$, and a ratio between the $K_{DR}$ and the $K_{DT}$ may be from about $10^2$ to $10^{12}$.

In some embodiments, the one or more nucleic acid agents identified as having a desired property binds to the target moiety with a first apparent $K_{DT}$ when the binding occurs in a composition comprising the target moiety but not the reference moiety, and the one or more nucleic acid agents identified as having the desired property binds to the target moiety with a second apparent $K_{DT}$ when the binding occurs in a composition comprising both the target moiety and the reference moiety, and wherein a difference between the first apparent $K_{DT}$ and the second apparent $K_{DT}$ may be less than about 20% of the value of the first apparent $K_{DT}$.

In some embodiments, the component for generating an enriched mixture of candidate nucleic acid agents comprises devices and/or agents for conducting nucleic acid amplification. For example, the nucleic acid amplification may comprise PCR or reverse transcriptase PCR.

In some embodiments, the kit further comprises an agent and/or a device for conducting emulsion PCR to immobilize the mixture of candidate nucleic acid agents onto the plurality of particle.

In some embodiments, the target moiety comprises a protein or a part thereof selected from the group consisting of Tumor Necrosis Factor α, Neutrophil Gelatinase-Associated Lipocalin, Histidine-Rich Protein 2, Platelet-Derived Growth Factors, Vascular Endothelial Growth Factors, Angiopoietins, Complement proteins and Integrins.

In some embodiments, the reference moiety comprises one or more molecules homologous to the target moiety. For example, the one or more molecules of the reference moiety may have a homology from about 50% to about 99% to the target moiety.

In some embodiments, the reference moiety comprises a mixture comprising proteins, glycans and/or small molecules. For example, the reference moiety may comprise a mixture comprising blood, plasma, serum, liquid humor, vitreous, urine, tissue fluid, spit, and/or saliva. In some embodiments, the blood, plasma, serum, liquid humor, vitreous, urine, tissue fluid, spit, and/or saliva is from a human being.

In another aspect, the present disclosure provides a pool of particles comprising from about $1 \times 10^2$ to about $1 \times 10^{14}$ particles. Each particle from the pool may have immobilized thereon from about $1 \times 10^2$ to about $1 \times 10^{10}$ copies of single stranded nucleic acid agents comprising a single nucleic acid sequence. Sequence diversity of the pool of particles may be less than the number of particles in the pool. Each particle from the pool may have at least one dimension of from about 50 nm to about 100 µm. The single stranded nucleic acid agents immobilized on the particles may bind to a target moiety with a $K_{DT}$ and binds to a reference moiety with a $K_{DR}$, the $K_{DT}$ may be from about 1 fM to about 1 µM and a ratio between the $K_{DR}$ and the $K_{DT}$ may be from about $10^2$ to $10^{12}$.

In some embodiments, the single stranded nucleic acid agents immobilized on the particles bind to the target moiety with a first apparent $K_{DT}$ when the binding occurs in a composition comprising the target moiety but not the reference moiety, and the single stranded nucleic acid agents immobilized on the particles bind to the target moiety with a second apparent $K_{DT}$ when the binding occurs in a composition comprising both the target moiety and the reference moiety, and wherein a difference between the first apparent $K_{DT}$ and the second apparent $K_{DT}$ may be less than about 20% of the value of the first apparent $K_{DT}$.

In some embodiments, the target moiety is a protein or a polypeptide moiety.

In some embodiments, the reference moiety is a protein or a polypeptide moiety.

In some embodiments, the reference moiety comprises serum proteins.

In some embodiments, the single stranded nucleic acid agent is selected from a DNA molecule, a RNA molecule, a chemically modified DNA molecule, and a chemically modified RNA molecule. For example, the single stranded nucleic acid agent may be a DNA molecule. In some embodiments, the single stranded nucleic acid agent is an aptamer. In some embodiments, the single stranded nucleic acid agent comprises one or more non-natural nucleic acid.

In some embodiments, one or more of the single stranded nucleic acid agents comprises a molecule conjugated thereto. For example, the molecule conjugated to one or more of the single stranded nucleic acids may be a small molecule, a fluorophore, a peptide, and/or an siRNA. In some embodiments, the desired property is an ability to specifically bind to a target or an activity induced by such specific binding. For example, the activity induced by such specific binding may be a catalytic activity, a modified catalytic activity, an inhibition activity, an activation activity, a modification of an inhibition activity, an activation activity, a structure switching activity, a modification of a structure switching activity, and/or a cooperative activity.

In some embodiments, the particle is non-magnetic, magnetic or paramagnetic. In some embodiments, each of the plurality of particles has at least one dimension of from about 50 nm to about 100 µm. For example, the plurality of particles may comprise carboxylic acid paramagnetic particles having an average diameter of about 1 µm.

In some embodiments, each of the single stranded nucleic acid agents is coupled to a particle of the pool via a linker. The linker may be a cleavable linker, a non-cleavable linker or a combination thereof. In some embodiments, the linker is an amino-modified nucleic acid primer.

In some embodiments, the target moiety comprises a protein or a part thereof selected from the group consisting of Tumor Necrosis Factor α, Neutrophil Gelatinase-Associated Lipocalin, Histidine-Rich Protein 2, Platelet-Derived Growth Factors, Vascular Endothelial Growth Factors, Angiopoietins, Complement proteins and Integrins.

In some embodiments, the reference moiety comprises one or more molecules homologous to the target moiety. For example, the one or more molecules of the reference moiety have a homology from about 50% to about 99% to the target moiety.

In some embodiments, the reference moiety comprises a mixture comprising proteins, glycans and/or small molecules. For example, the reference moiety may comprise a mixture comprising blood, plasma, serum, liquid humor, vitreous, urine, tissue fluid, spit, and/or saliva. In some embodiments, the blood, plasma, serum, liquid humor, vitreous, urine, tissue fluid, spit, and/or saliva is from a human being.

In some embodiments, the target moiety comprises Tumor Necrosis Factor α or a part thereof, and the single stranded nucleic acid agents immobilized on the particles may comprise a sequence as set forth in SEQ ID NO: 1.

In some embodiments, the target moiety comprises Neutrophil Gelatinase-Associated Lipocalin or a part thereof, and the single stranded nucleic acid agents immobilized on the particles may comprise a sequence as set forth in SEQ ID NO: 3.

For example, the target moiety comprises Histidine-Rich Protein 2 or a part thereof, and the single stranded nucleic acid agents immobilized on the particles may comprise a sequence as set forth in SEQ ID NO: 4.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are employed, and the accompanying drawings (also "figure" and "FIG." herein), of which:

DETAILED DESCRIPTION

Figure 1:
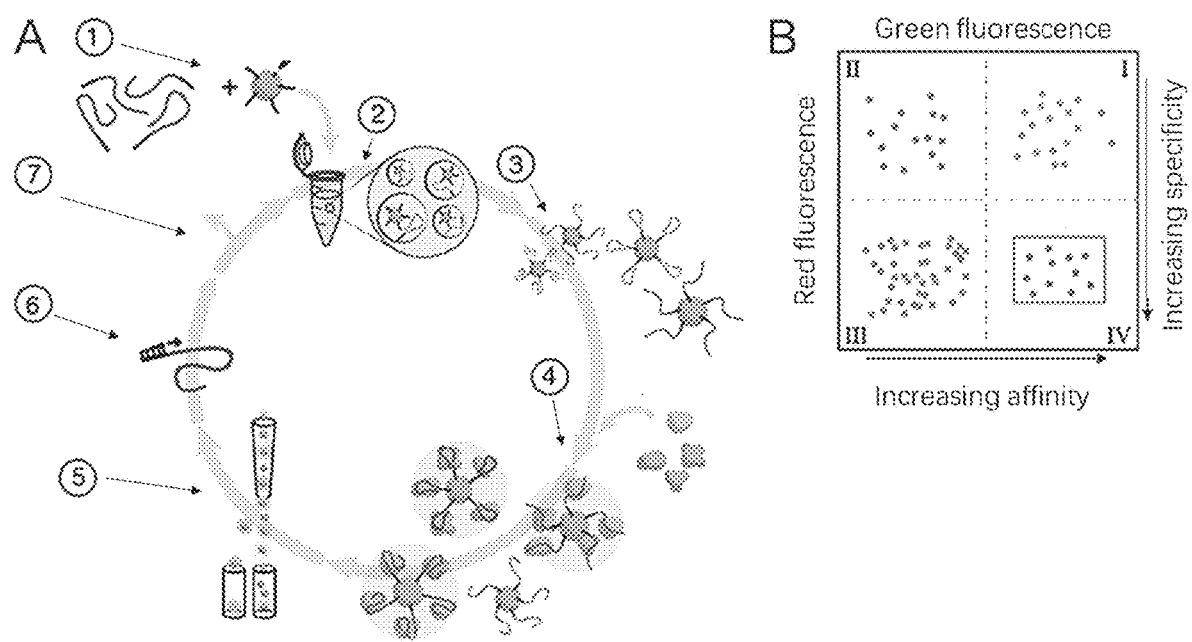
FIGS. 1A-1B provide an illustration of a method of the present application.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "substantial", as used herein, generally refers to more than a minimal or insignificant amount; and "substantially" generally refers to more than minimally or insignificantly. The term "a substantial part of", as used herein, generally refers to an amount, quantity, sequence, length, concentration etc. of a part of an object that is at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99% of that of the entire amount, quantity, sequence, length, concentration etc. of the corresponding object.

The term "nucleic acid agent", as used herein, generally refers to a molecule comprising one or more nucleic acid subunits (e.g., nucleotide). A nucleic acid agent may include one or more subunits selected from adenosine (A), cytosine (C), guanine (G), thymine (T) and uracil (U), or analogs and variants thereof. A nucleotide can include A, C, G, T or U, or analogs and variants thereof including but not limited to peptide nucleic acid (PNA), phosphorothioated, Locked Nucleic Acids (LNA's), a 2'-O-Methyl (2'OMe) modified nucleotides, a 2'-O-(2-Methoxyethyl) (2'-O-MOE) modified nucleotides, 2' Fluoro modified nucleotides, and a 5' Inverted Dideoxy-T. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). A subunit can enable individual nucleic acid bases or groups of bases (e.g., AA, TA, AT, GC, CG, CT, TC, GT, TG, AC, CA, or uracil-counterparts thereof) to be resolved. In some examples, a nucleic acid agent is deoxyribonucleic acid (DNA) or ribonucleic acid (RNA), or derivatives thereof. A nucleic acid agent may be single-stranded or double stranded. A nucleic acid agent may comprise one or more modified nucleotides, e.g., methylated nucleotides and nucleotide analogs.

The modified nucleotide may comprise one or more chemical modifications at one or more positions independently selected from the group consisting of a ribose position, a deoxyribose position, a phosphate position, and a base position. For example, the chemical modifications are independently selected from the group consisting of a 2'-position sugar modification, a 2'-amino (2'-NH2) modification, a 2'-fluoro (2'-F) modification, a 2'-O-methyl (2'-OMe) modification, a 2'-O-(2-Methoxyethyl) (2'-O-MOE) modification, a 5-position modified pyrimidine, a modification at a cytosine exocyclic amine, a substitution of 5-bromouracil, a substitution of 5-bromodeoxyuridine, a substitution of 5-bromodeoxycytidine, a backbone modification, methylation, a 3' cap, and a 5' cap. The 5-position modified pyrimidine may be selected from the group consisting of 5-Carboxy-2'-deoxyuridine, 5-Aminoallyl-2'-deoxyuridine, 5-[(3-Indolyl)propionamide-N-allyl]-2'-deoxyuridine, 5-Carboxy-2'-deoxycytidine, 5-Aminoallyl-2'-deoxycytidine, Biotin-16-Aminoallyl-2'-deoxycytidine, 5-(N-benzyl carboxyamide)-2'-deoxyuridine, 5-(N), 5-Aminoallyl-2'-deoxycytidine (5-AA-dC), Biotin-16-Aminoallyl-2'-deoxycytidine (Biotin-16-AA-dC), 5-(N-benzyl carboxyamide)-2'-deoxyuridine, 5-(N-isobutyl carboxyamide)-2'-deoxyuridine, 5-(N-naphthyl methyl carboxyamide)-2'-deoxyuridine, and 5-(N-tryptamino carboxyamide)-2'-deoxyuridine.

As used herein, two or more "nucleic acid agents" are the same only when: 1) they have the same nucleic acid sequences; and 2) each nucleotide in one nucleic acid agent is the same as the corresponding nucleotide in the other nucleic acid agents. In this regard, a nucleotide and its modified version, its analogue or other variants thereof are considered as different nucleotides. Accordingly, if two nucleic acid agents comprise the same nucleic acid sequence while one comprises only unmodified A, C, G, T or U, and the other one comprises modified A, C, G, T or U, they are considered different nucleic acid agents.

The term "polymerase," as used herein, generally refers to any enzyme capable of catalyzing a polymerization reaction. Examples of polymerases include, without limitation, a nucleic acid polymerase, a transcriptase or a ligase. A polymerase can be a polymerization enzyme or a polymerizing enzyme.

The term "aptamer" or "aptamer sequence", as used herein, generally refers to a nucleic acid having a specific binding affinity for a target, e.g., a target molecule, wherein such target is other than a polynucleotide that binds to said nucleic acid through a mechanism which predominantly depends on Watson/Crick base pairing.

The terms "peptide", "polypeptide" and "protein", used interchangeably herein, generally refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.

The term "sequence" as used, for example, in the context of a nucleic acid sequence (e.g., an aptamer sequence) or an amino acid sequence, generally refers to the primary structure, e.g., the order of monomeric subunits (e.g., nucleotides or amino acids). As used herein, sequences (e.g., nucleic acid sequences) with substantially identical order of monomeric subunits are considered the same sequence.

For example, in terms of nucleic acid agents, if the order of A (or analogues, variants, derivatives thereof), C (or analogues, variants, derivatives thereof), T (or analogues, variants, derivatives thereof), G (or analogues, variants, derivatives thereof) and U (or analogues, variants, derivatives thereof) is the same in their sequences, these nucleic acid agents are considered as having the same sequence.

In some cases, two molecules (e.g., nucleic acid agents) may have the same order of monomeric subunits (e.g., the order of A (or analogues, variants, derivatives thereof), C (or analogues, variants, derivatives thereof), T (or analogues, variants, derivatives thereof), G (or analogues, variants, derivatives thereof) and U (or analogues, variants, derivatives thereof)), while one comprises unmodified subunits and the other one comprises the corresponding modified subunits, in this case, these two molecules are considered two different molecules (e.g., nucleic acid agents) with the same sequence (e.g., nucleic acid sequence). For example, a modified A is the corresponding modified nucleotide of the nucleotide A, a modified C is the corresponding modified nucleotide of the nucleotide C, a modified T is the corresponding modified nucleotide of the nucleotide T, a modified G is the corresponding modified nucleotide of the nucleotide G, and a modified U is the corresponding modified nucleotide of the nucleotide U.

The terms "label" and "detectable label" may be used interchangeably herein, and generally refer to a molecule capable of being detected, including, but not limited to, antibodies (e.g., labeled antibodies, such as fluorescently labeled antibodies), radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, streptavidin or haptens) and the like.

The term "fluorescer" as used herein, generally refers to a substance or a portion thereof which is capable of exhibiting fluorescence in the detectable range. Exemplary detectable moieties suitable for use as detectable labels may include e.g., affinity tags and fluorescent proteins.

The term "amplification", as used herein, generally refers to an increase in copy number of a nucleic acid, and it includes the generation of DNA from RNA. The amplification may be performed by any known method. The amplification method may require thermal cycling or may be performed at isothermal conditions. For example, the amplification may include polymerase chain reaction (PCR), nucleic acid sequence-based amplification (NASBA), ligase chain reaction (LCR), strand displacement amplification (SDA), rolling circle amplification (RCA), or a combination thereof. The amplification method may also include a method of RNA amplification, for example, reverse transcription (RT) or RT-PCR. Additionally, the amplification may be DNA amplification or RNA amplification. The nucleic acid amplification may be, for example, a real-time nucleic acid amplification.

The term "PCR", as used herein, generally refers to a method of amplifying a target nucleic acid with one or more primers that specifically binds to a target nucleic acid, e.g, by using a polymerase. For example, the amplification of a nucleic acid by PCR may comprise repeated cycles of denaturation, annealing, and elongation.

The term "emulsion PCR", as used herein, generally refers to a PCR reaction conducted in an emulsion comprised in a micro-reactor or a compartment (e.g., a droplet, such as a water-in-oil droplet or compartment) to generate a plurality of copies of a template molecule.

The term "target", as used herein, generally refers to an object to be detected. For example, a target may be a protein (e.g., an antibody), a polynucleotide, a polypeptide, a virus, a microorganism, a small molecule, a whole cell, a cellular component, a liposome, or a combination thereof. In some embodiments, suitable target may include, for example, small molecules (e.g., organic dyes), amino acids, carbohydrates, lipids, aminoglycosides, antibiotics, peptides, proteins, post-translational modification, nucleic acids, virus, whole cells and/or cellular components. Small molecule targets of interest generally may have a molecular weight of about 800 Daltons or less. Protein targets of interest may include, for example, cell surface receptors, signal transduction factors, and hormones. Cellular targets of interest may include, for example, mammalian cells, particularly human cells, stem cells, tumor cells and bacterial cells. In some embodiments, two or more types of targets (such as protein targets having different amino acid sequences) may be simultaneously tested against a single library of candidate nucleic acid agents or candidate aptamer sequences. In some embodiments, a target or a molecule associated with a target, e.g., via a binding interaction, may be detectably labeled.

The term "affinity", as used herein, generally refers to the strength of the sum total of non-covalent interactions between a single binding site of a molecule (e.g., an aptamer) and its binding partner (e.g., a protein).

The term "$K_D$" or "$K_D$ value", as used herein, generally refers to a dissociation constant, measured by a technique appropriate for the candidate nucleic acid agent and binding partner pair, for example by using Ligand Binding Assays with radioactive or fluorescent measurement, Surface Plasmon Resonance (SPR), Bio-Layer Interferometry (BLI, e.g., the Octet® Systems), SRU biosystems BIND®, Isothermal Titration Calorimetry (ITC), or Microscale Thermophoresis (MST). In some embodiments, the $K_D$ value is determined using a standard fluorescence-based ligand binding assay and saturation analysis. In one example, various concentrations of fluorescently labeled binding partner molecules (e.g., target molecules or reference moiety molecules) were incubated with a particle of the present disclosure for at least 3 hours at room temperature with gentle rotation. Each sample was then washed, and the remaining bound binding partner was quantified by measuring the fluorescence of each particle using a flow cytometer. The background-subtracted fluorescence values were then fit to a saturation binding curve, e.g. by using an equilibrium binding model (for example, according to the law of mass action).

The term "$K_{DT}$" or "$K_{DT}$ value", as used herein, generally refers to a dissociation constant, measured by a technique appropriate for the candidate nucleic acid molecule and target pair, for example by using Ligand Binding Assays with radioactive or fluorescent measurement, Surface Plasmon Resonance (SPR), Bio-Layer Interferometry (BLI, e.g., the Octet® Systems), SRU biosystems BIND®, Isothermal Titration Calorimetry (ITC), or Microscale Thermophoresis (MST). In some embodiments, the $K_{DT}$ value is determined using a standard fluorescence-based ligand binding assay and saturation analysis. In one example, various concentrations of fluorescently labeled target molecules were incubated with a particle of the present disclosure for at least 3 hours at room temperature with gentle rotation. Each sample was then washed, and the remaining bound target was quantified by measuring the fluorescence of each particle using a flow cytometer. The background-subtracted fluorescence values were then fit to a saturation binding curve, e.g. by using an equilibrium binding model (for example, according to the law of mass action). In the present application, the $K_{DT}$ may be at least about 100 µM, at least about 50 µM, at least about 10 µM, at least about 1 µM, at least about 500 nM, at least about 100 nM, at least about 50 nM, at least about 10 nM, at least about 8 nM, at least about 6 nM, at least about 4 nM, at least about 2 nM, at least about 1 nM, at least about 900 pM, at least about 800 pM, at least about 700 pM, at least about 600 pM, at least about 500 pM, at least about 400 pM, at least about 300 pM, at least about 200 pM, at least about 100 pM, at least about 90 pM, at least about 80 pM, at least about 70 pM, at least about 60 pM, at least about 50 pM, at least about 40 pM, at least about 30 pM, at least about 20 pM, at least about 10 pM, at least about 5 pM, at least about 1 pM, at least about 500 fM, at least about 100 fM, at least about 50 fM, at least about 10 fM, at least about 5 fM, at least about 1 fM, or greater.

The term "$K_{DR}$" or "$K_{DR}$ value", as used herein, generally refers to a dissociation constant, measured by a technique appropriate for the candidate nucleic acid molecule and reference moiety pair, for example by using Ligand Binding Assays with radioactive or fluorescent measurement, Surface Plasmon Resonance (SPR), Bio-Layer Interferometry (BLI, e.g., the Octet® Systems), SRU biosystems BIND®, Isothermal Titration Calorimetry (ITC), or Microscale Thermophoresis (MST). In some embodiments, the $K_{DR}$ value is determined using a standard fluorescence-based ligand binding assay and saturation analysis. In one example, various concentrations of fluorescently labeled reference moiety molecules were incubated with a particle of the present disclosure for at least 3 hours at room temperature with gentle rotation. Each sample was then washed, and the remaining bound reference moiety was quantified by measuring the fluorescence of each particle using a flow cytometer. The background-subtracted fluorescence values were then fit to a saturation binding curve, e.g. by using an equilibrium binding model (for example, according to the law of mass action).

The terms "specificity", "specific binding", "specifically binds to" and "specific for" are used interchangeably herein and generally refer to the binding of an agent (e.g., a nucleic acid agent, such as an aptamer) to a target molecule (e.g., a protein or a part thereof), and the binding is measurably and/or statistically different from a non-specific interaction (e.g., a non-specific interaction may be binding to a reference molecule or a random molecule). For example, in the present application, the specificity of a candidate nucleic acid agent binding to a corresponding target moiety may be represented as the ratio of $K_{DR}/K_{DT}$. The $K_{DR}/K_{DT}$ ratio may be from about $10^2$ to $10^{12}$, e.g., from about $10^3$ to $10^{12}$, from about $10^4$ to $10^{12}$, from about $10^5$ to $10^{12}$, from about $10^6$ to $10^{12}$, from about $10^7$ to $10^{12}$, from about $10^8$ to $10^{12}$, from about $10^9$ to $10^{12}$, from about $10^{10}$ to $10^{12}$, from about $10^{11}$ to $10^{12}$.

The terms "conjugate", "conjugated" and "conjugation" may be used interchangeably and generally refer to any and all forms of covalent or non-covalent linkage, and include, without limitation, direct genetic or chemical fusion, coupling through a linker or a cross-linking agent, and non-covalent association.

The term "immobilized", as used herein, generally refers to attaching or fixing of a molecule or an agent to a substrate or a support (e.g., a particle).

The term "therapeutically active component", as used herein, generally refers to a molecule or an agent showing a therapeutic effect, e.g., for the treatment or control of disease progression.

The term "enriched", as used herein, generally refers to an increase of the amount, quantity or percentage of one or more particular objects within a population.

The term "target binding activity", as used herein, generally refers to an ability to bind to a specific target. For example, a "target binding activity" may be affinity, specificity or bi-specificity.

The term "target-binding induced activity", as used herein, generally refers to an ability induced or caused by the binding of a molecule or agent to an intended target. A "target-binding induced activity" may comprise a catalytic activity, an inhibition activity, an activation activity, a structure switching activity, and/or a cooperative activity.

The term "sequencing", as used herein, generally refers to a process or reaction for determining the sequence (e.g., order of monomeric subunits, such as order of nucleotides) of a molecule (e.g., a nucleic acid agent).

The term "identity", as used herein, generally refers to information that uniquely distinguishes a molecule or agent from the other molecules or agents. For example, an identity of a nucleic acid molecule may be determined or represented by its nucleic acid sequences and/or the nucleotides it comprises.

The term "natural nucleic acid", as used herein, generally refers to nucleic acids occurring in nature. The term "natural DNA", as used herein, generally refers to DNA nucleic acids occurring in nature. In some embodiments, "natural nucleic acid" also comprises synthesized or modified nucleotides not impeding amplification and/or sequencing.

The term "consists essentially of", as used herein, generally refers to a substantial part being made of the indicated components or ingredients.

The term "homologous", as used herein, generally refers to amino acid sequences and/or nucleotide sequences having certain degree of sequence similarities and/or identities. For example, two homologous molecules may have a sequence homology of at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99%. For example, the homology may be from about 25% to about 99%, from about 30% to about 99%, from about 35% to about 99%, from about 40% to about 99%, from about 45% to about 99%, from about 50% to about 99%, from about 55% to about 99%, from about 60% to about 99%, from about 65% to about 99%, from about 70% to about 99%, from about 75% to about 99%, from about 80% to about 99%, from about 85% to about 99%, from about 90% to about 99%, from about 95% to about 99%, or higher.

As used herein, the terms "determining," "measuring," "assessing," and "assaying" are used interchangeably herein and include both quantitative and qualitative determination of a value or a parameter, unless the context clearly indicates otherwise.

The term "about", when used in the context of numerical values, generally refers to a value less than 1% to 15% (e.g., less than 1%, less than 2%, less than 3%, less than 4%, less than 5%, less than 6%, less than 7%, less than 8%, less than 9%, less than 10%, less than 11%, less than 12%, less than 13%, less than 14%, or less than 15%) above or below an indicated value.

Where a range of values (e.g., a numerical range) is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

As used herein, the singular forms "a," "and," and "the" include plural referents unless the context clearly dictates otherwise. Thus, for example, reference to "a particle" includes a plurality of such particles and reference to "the sequence" includes reference to one or more said sequences and equivalents thereof known to those skilled in the art, and so forth.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. This is intended to provide support for all such combinations.

The present disclosure provides a method, a kit and/or a pool of particles for conducting or for being employed in Multi-Parameter Particle Display (MPPD). The method, kit or pool of particles according to the present application provides a means for simultaneously screening for nucleic acid agents having both high affinity and specificity in a high-throughput manner.

In one aspect, the present disclosure provides a method for identifying one or more nucleic acid agents having a desired property from a mixture of candidate nucleic acid agents. The mixture of candidate nucleic acid agents may comprise a plurality of single stranded nucleic acids. The method may comprise: a) providing a plurality of particles with the candidate nucleic acid agents immobilized thereon, wherein each of the plurality of particles may comprise at most a subset of the candidate nucleic acid agents within the mixture. In some cases, the method may also comprise immobilizing the mixture of candidate nucleic acid agents onto the plurality of particles, wherein each of the plurality of particles may comprise at most a subset of the candidate nucleic acid agents within the mixture.

Subsequent to a), the method may further comprise b) exposing the plurality of particles to a screening composition comprising a target moiety and a reference moiety. An interaction of the candidate nucleic acid agents with the target moiety may be indicated by a first signal, an interaction of the candidate nucleic acid agents with the reference moiety may be indicated by a second signal, and an intensity of the first signal together with an intensity of the second signal for a particular particle may provide a sorting parameter of the particular particle. For example, in the screening composition, a concentration of the target moiety and a concentration of the reference moiety may be respectively set at a value enabling the sorting parameter of about 0.05% to about 1% of the plurality of particles to be within a predetermined sorting range. For example, by changing the concentration of the target moiety and/or the reference moiety, the percentage of particles having a sorting parameter within the predetermined sorting range may vary accordingly, and when about 0.05% to about 1% (e.g., about 0.05% to about 0.08%, about 0.05% to about 0.1%, about 0.05% to about 0.12%, about 0.05% to about 0.15%, about 0.05% to about 0.2%, about 0.05% to about 0.25%, about 0.05% to about 0.3%, about 0.05% to about 0.35%, about 0.05% to about 0.4%, about 0.05% to about 0.45%, about 0.05% to about 0.5%, about 0.05% to about 0.55%, about 0.05% to about 0.6%, about 0.05% to about 0.65%, about 0.05% to about 0.7%, about 0.05% to about 0.75%, about 0.05% to about 0.8%, about 0.05% to about 0.85%, about 0.05% to about 0.9%, about 0.05% to about 0.95%, etc.) of the particles have a sorting parameter within the predetermined sorting range, the concentration of the target moiety and that of the reference moiety are considered as appropriate for performing the method of the present application.

Subsequent to b), the method may further comprise c) isolating from the plurality of particles one or more selected particles having a sorting parameter within the predetermined sorting range. The one or more selected particles may comprise one or more nucleic acid agents having the desired property.

Subsequent to c), the method may further comprise d) identifying the one or more nucleic acid agents having the desired property from the one or more selected particles.

In another aspect, the present disclosure provides a kit, which may be used for identifying one or more nucleic acid agents having a desired property from a mixture of candidate nucleic acid agents. The mixture of candidate nucleic acid agents may comprise a plurality of single stranded nucleic acids. The kit may comprise: a plurality of particles; a mixture of candidate nucleic acid agents to be immobilized onto the plurality of particles; and a screening composition for screening the plurality of particles with the mixture of candidate nucleic acid agents immobilized thereon. The screening composition may comprise a target moiety and a reference moiety, a concentration of the target moiety and a concentration of the reference moiety in the screening composition may be adjustable to enable sorting out of selected particles with the one or more nucleic acid agents having the desired property immobilized thereon. A percentage of the selected particles may be from about 0.05% to about 0.25% of the plurality of particles screened. In some cases, the kit may comprise, in addition or alternatively, a plurality of particles with the candidate nucleic acid agents immobilized thereon and the screening composition, wherein each of the plurality of particles may comprise at most a subset of the candidate nucleic acid agents within the mixture.

In the screening composition, the concentration of the target moiety and the concentration of the reference moiety may be adjusted respectively, so that about 0.05% to about 1% of the plurality of particles may be selected as particles with the one or more nucleic acid agents having the desired property immobilized thereon. For example, by changing the concentration of the target moiety and/or the reference moiety, the percentage of the selected particles may vary accordingly, and when about 0.05% to about 1% (e.g., about 0.05% to about 0.08%, about 0.05% to about 0.1%, about 0.05% to about 0.12%, about 0.05% to about 0.15%, about 0.05% to about 0.2%, about 0.05% to about 0.25%, about 0.05% to about 0.3%, about 0.05% to about 0.35%, about 0.05% to about 0.4%, about 0.05% to about 0.45%, about 0.05% to about 0.5%, about 0.05% to about 0.55%, about 0.05% to about 0.6%, about 0.05% to about 0.65%, about 0.05% to about 0.7%, about 0.05% to about 0.75%, about 0.05% to about 0.8%, about 0.05% to about 0.85%, about 0.05% to about 0.9%, about 0.05% to about 0.95%, etc.) of the particles are selected, the concentration of the target moiety and that of the reference moiety in the screening composition are considered as appropriate.

In another aspect, the present disclosure provides a pool of particles comprising about $1 \times 10^2$ to about $1 \times 10^{14}$ particles. Each particle from the pool may have immobilized thereon from about $1 \times 10^2$ to about $1 \times 10^{10}$ copies of single stranded nucleic acid agents comprising a single nucleic acid sequence. The sequence diversity of the pool of particles may be less than the number of particles in the pool. Each particle from the pool may have at least one dimension of from about 50 nm to about 100 µm.

In the present application, the candidate nucleic acid agents may be represented by a mixture of nucleic acid agents which are regarded as candidates for the selection of nucleic acid agents with both high affinity and specificity. For example, the candidate nucleic acid agents may comprise single stranded nucleic acid agents. In some embodiments, the candidate nucleic acid agent comprises or is selected from a DNA molecule, a RNA molecule, a chemically modified DNA molecule, a chemically modified RNA molecule, and/or a mixture thereof. For example, the candidate nucleic acid agent may comprise a single-stranded DNA molecule. In some embodiments, the candidate nucleic acid agent comprises or is an aptamer. As used in the present application, a DNA molecule may comprise natural or non-natural nucleotides. In some embodiments, the candidate nucleic acid agent comprises one or more non-natural nucleic acid.

Suitable candidate nucleic acid agents for use in connection with the disclosed methods, kits and pool of particles according to the present application may include nucleic acids, e.g., single stranded nucleic acids. The candidate nucleic acid agents may be provided in the form of combinatorial candidate nucleic acid agent libraries which include a large number of at least partially random nucleic acid sequences. The candidate nucleic acid agent libraries may include, for example, from about $1 \times 10^2$ to about $1 \times 10^{14}$ unique candidate nucleic acid agent sequences, e.g., from about $1 \times 10^3$ to about $1 \times 10^{14}$ unique sequences, from about $1 \times 10^4$ to about $1 \times 10^{14}$ unique sequences, from about $1 \times 10^5$ to about $1 \times 10^{14}$ unique sequences, from about $1 \times 10^6$ to about $1 \times 10^{14}$ unique sequences, from about $1 \times 10^7$ to about $1 \times 10^{14}$ unique sequences, from about $1 \times 10^8$ to about $1 \times 10^{14}$ unique sequences, from about $1 \times 10^9$ to about $1 \times 10^{14}$ unique sequences, from about $1 \times 10^{10}$ to about $1 \times 10^{14}$ unique sequences, from about $1 \times 10^{11}$ to about $1 \times 10^{14}$ unique sequences, from about $1 \times 10^{12}$ to about $1 \times 10^{14}$ unique sequences, or from about $1 \times 10^{13}$ to about $1 \times 10^{14}$ unique sequences.

The candidate nucleic acid agents according to the present application may include nucleic acid sequences from about 20 to about 150 nucleotides in length, e.g., from about 40 to about 130 nucleotides in length, from about 50 to about 120 nucleotides in length, from about 60 to about 110 nucleotides in length, from about 70 to 100 nucleotides in length, or from about 80 to about 90 nucleotides in length. The candidate nucleic acid agents may comprise random nucleic acid sequences of from about 20 nucleotides in length to about 70 nucleotides in length, e.g., from about 40 nucleotides in length to about 60 nucleotides in length. In addition to random nucleic acid sequence regions, the candidate nucleic acid agents may include nucleic acid sequences comprising flanking regions containing primer binding sites.

The candidate nucleic acid agents according to the present application may include deoxyribonucleotides, ribonucleotides, and/or analogs thereof, and may include naturally occurring nucleotides and/or modified nucleotides. For example, the candidate nucleic acid agents may include 2'-fluoro-modified RNA, 2'-O-methyl-modified RNA, and/or chemically modified DNA. The chemically modified DNA may comprise one or more modified nucleotide. The modified nucleotide may comprise one or more chemical modifications at one or more positions independently selected from the group consisting of a ribose position, a deoxyribose position, a phosphate position, and a base position. For example, the chemical modifications are independently selected from the group consisting of a 2'-position sugar modification, a 2'-amino (2'-NH2) modification, a 2'-fluoro (2'-F) modification, a 2'-O-methyl (2'-OMe) modification, a 2'-O-(2-Methoxyethyl) (2'-O-MOE) modification, a 5-position modified pyrimidine, a modification at a cytosine exocyclic amine, a substitution of 5-bromouracil, a substitution of 5-bromodeoxyuridine, a substitution of 5-bromodeoxycytidine, a backbone modification, methylation, a 3' cap, and a 5' cap. The 5-position modified pyrimidine may be selected from the group consisting of 5-Carboxy-2'-deoxyuridine, 5-Aminoallyl-2'-deoxyuridine, 5-[(3-Indolyl)propionamide-N-allyl]-2'-deoxyuridine, 5-Carboxy-2'-deoxycytidine, 5-Aminoallyl-2'-deoxycytidine, Biotin-16-Aminoallyl-2'-deoxycytidine, 5-(N-benzyl carboxyamide)-2'-deoxyuridine, 5-(N), 5-Aminoallyl-2'-deoxycytidine (5-AA-dC), Biotin-16-Aminoallyl-2'-deoxycytidine (Biotin-16-AA-dC), 5-(N-benzyl carboxyamide)-2'-deoxyuridine, 5-(N-isobutyl carboxyamide)-2'-deoxyuridine, 5-(N-naphthyl methyl carboxyamide)-2'-deoxyuridine, and 5-(N-tryptamino carboxyamide)-2'-deoxyuridine.

In some embodiments, one or more of the candidate nucleic acid agents comprises a molecule conjugated thereto. For example, the molecule conjugated may be selected from the group consisting of a protein (such as an antibody), a small molecule, a fluorophore, a peptide, a therapeutically active component (e.g., a drug), a polymer (e.g., polyethylene glycol, poly (lactic-co-glycolic acid), or hydrogel), and an siRNA.

A variety of suitable particles may be used according to any aspect of the present disclosure. Such particles may be sized to have at least one dimension, e.g., diameter, of from about 50 nm to about 100 µm. For example, in some embodiments a suitable particle is sized to have at least one dimension of from about 50 nm to about e.g., from about 50 nm to about 500 nm, or from about 50 nm to about 100 nm. In other embodiments, a suitable particle is sized to have at least one dimension of from about 500 nm to about 100 µm, e.g., from about 1 µm to about 100 µm, or from about 50 µm to about 100 µm. Suitable particles may be generally spherical or may have any other suitable shape.

The particles to be used according to any aspect of the present disclosure may be made from a variety of suitable materials. For example, magnetic particles may be utilized in the disclosed methods and compositions. Suitable magnetic particles may include, for example, magnetic beads or other small objects made from a magnetic material such as a ferromagnetic material, a paramagnetic material, or a superparamagnetic material. Magnetic particles may include, e.g., iron oxide ($Fe_2O_3$ and/or $Fe_3O_4$). Additional particles of interest may include polymer based particles, e.g., polymer based beads. For example, polystyrene particles may be utilized. In addition, in some embodiments ceramic particles may be utilized.

The particles to be used according to any aspect of the present disclosure may include or be coated with a material which facilitates coupling of the particles to the candidate nucleic acid agents. Examples of coatings may include polymer shells, glasses, ceramics, gels, etc. In some embodiments, the coatings include or are themselves coated with a material that facilitates coupling or physical association of the particles with the candidate nucleic acid agents. For example, particles with exposed carboxylic acid groups may be used for attachment to candidate nucleic acid agents.

In some embodiments, the plurality of particles comprises carboxylic acid paramagnetic particles having an average diameter of about 50 nm to about 100 µm (such as 1 µm). In some embodiments, the plurality of particles comprises primer-conjugated magnetic particles. The primer may be suitable for performing emulsion PCR.

The plurality of particles may comprise from about $1 \times 10^2$ to about $1 \times 10^{14}$ particles, e.g., from about $1 \times 10^3$ to about $1 \times 10^{14}$ particles, from about $1 \times 10^4$ to about $1 \times 10^{14}$ particles, from about $1 \times 10^5$ to about $1 \times 10^{14}$ particles, from about $1 \times 10^6$ to about $1 \times 10^{14}$ particles, from about $1 \times 10^7$ to about $1 \times 10^{14}$ particles, from about $1 \times 10^8$ to about $1 \times 10^{14}$ particles, from about $1 \times 10^9$ to about $1 \times 10^{14}$ particles, from about $1 \times 10^{10}$ to about $1 \times 10^{14}$ particles, from about $1 \times 10^{11}$ to about $1 \times 10^{14}$ particles, from about $1 \times 10^{12}$ to about $1 \times 10^{14}$ particles, or from about $1 \times 10^{13}$ to about $1 \times 10^{14}$ particles.

In some embodiments, multiple copies of a single candidate nucleic acid agent are or to be immobilized on the plurality of particles. The candidate nucleic acid agent immobilized on any one particle of the plurality of particles may be different from that on at least one other particles. In some embodiments, the candidate nucleic acid agent immobilized on any one particle of the plurality of particles is different from that on any other particles. In the present application, multiple copies of a candidate nucleic acid agent may comprise identical copies of a specific candidate nucleic acid. Each particle of the plurality of particles may comprise from about $1 \times 10^2$ to about $1 \times 10^{10}$ candidate nucleic acid agents bound thereon, e.g., from about $1 \times 10^2$ to about $1 \times 10^{10}$ candidate nucleic acid agents, from about $1 \times 10^3$ to about $1 \times 10^{10}$ candidate nucleic acid agents, from about $1 \times 10^4$ to about $1 \times 10^{10}$ candidate nucleic acid agents, from about $1 \times 10^5$ to about $1 \times 10^{10}$ candidate nucleic acid agents, from about $1 \times 10^6$ to about $1 \times 10^{10}$ candidate nucleic acid agents, from about $1 \times 10^7$ to about $1 \times 10^{10}$ candidate nucleic acid agents, from about $1 \times 10^8$ to about $1 \times 10^{10}$ candidate nucleic acid agents, from about $1 \times 10^9$ to about $1 \times 10^{10}$ candidate nucleic acid agents.

The candidate nucleic acid agents may be immobilized onto the plurality of particles in a variety of ways. In some embodiments, each of the candidate nucleic acid agents is coupled to a particle of the plurality of particles via a linker, such as a cleavable linker, a non-cleavable linker or a combination thereof. In some embodiments, the linker is an amino-modified nucleic acid primer. For example, the candidate nucleic acid agents may be attached to a particle having exposed carboxylic acid groups using amino group modification. For example, 5'-amino modified oligonucleotides may be used in connection with carbodiimide mediated amide bond formation to attach candidate nucleic acid agents to the particles. Carbodiimide mediated coupling methods are described in greater detail, for example, in Nakajima N. and Ikade Y. (1995) Bioconjugate Chem., 6(1):123-130; Gilles et al. (1990) *Anal Biochem.,* 184(2): 244-248; Sehgal D. and Vijay I K. (1994) *Anal Biochem.* 218(1): 87-91; and Szajani et al. (1991) *Appl Biochem Biotechnol.* 30(2):225-231.

In some embodiments, primer based enrichment methods such as PCR (e.g., emulsion PCR), reverse transcriptase PCR, or primer extension are utilized to provide particle-immobilized candidate nucleic acid agents. For example, nucleic acid primers may be attached to the particles using carbodiimide mediated coupling to facilitate these methods. Alternatively, biotin labeled primers may be utilized with streptavidin-coated particles to provide primer-coated beads.

In some embodiments of the method, the enrichment of the candidate nucleic acid agents is by a method of nucleic acid amplification. For example, the method of nucleic acid amplification may comprise PCR or reverse transcriptase PCR. In some embodiments of the method, the candidate nucleic acid agents are immobilized onto the particles with emulsion PCR. Generally, emulsion PCR as used according to the method of the present disclosure isolates individual template DNA molecules, e.g., from a combinatorial library, along with primer-coated particles, e.g., beads, in aqueous droplets within an oil phase. PCR amplification then coats each bead with clonal copies of the DNA molecule. After breaking the emulsion and removing unreacted PCR reagents, hybridized strands may be de-hybridized and particles with candidate nucleic acid agents immobilized thereon may be collected for subsequent screening.

When the candidate nucleic acid agents include RNA sequences, a modified version of the emulsion PCR method may be utilized. For example, a random DNA library may be synthesized, which represents the template of the candidate RNA nucleic acid agents. The DNA library can be paired with a complementary primer sequence and the reverse strand can be extended to form a double-stranded library which can initiate transcription. An emulsion can be prepared with the library, the transcription reagents, and a particle coated with sequences that can hybridize with the RNA transcripts by base-pairing. The emulsion can be prepared such that each emulsion droplet will only contain one or a few DNA templates, and the RNA transcript from that one or a few templates will be captured by the respective particles to form a particle-immobilized candidate RNA nucleic acid agent library.

In another approach, particle-immobilized candidate DNA nucleic acid agents can be synthesized as described previously herein using emulsion PCR. Then, a second emulsion can be prepared with the particle-immobilized candidate DNA nucleic acid agents, transcription reagents, and a second set of particles that contain sequences that can hybridize with RNA by base-pairing. The emulsion can be prepared such that each emulsion droplet will only contain one or a few particle-immobilized candidate DNA nucleic acid agents and their corresponding RNA transcripts. The RNA transcripts can be captured by the second set of particles to form a particle-immobilized candidate RNA nucleic acid agent library.

When the candidate nucleic acid agents include non-natural nucleic acids, a modified version of the emulsion PCR method may be utilized. For example, in a first step, starting from a non-natural nucleic acid sequence as template, a DNA primer sequence and natural A/T/C/G building blocks are used to PCR amplify the sequence into an amplified pool of natural DNA sequences (the amplified DNA will have the same sequence as the template, but not the non-natural composition). In order to obtain amplified non-natural nucleic acid sequences on particles, the natural DNA sequences derived from first step can be used as template in an emulsion reaction. A primer positioned on the particles can be used to pair with the template, and a polymerase capable of incorporating non-natural nucleic acids can be used to incorporate non-natural nucleic acid building blocks to extend the primer to a full-length complementary sequences. Suitable polymerases are known in the art. In addition, methods of identifying such polymerases are known in the art. See, for example, Lutz et al. Nucleic Acids Research, 1999, Vol. 27, No. 13, pp. 2792-2798, the disclosure of which is incorporated by reference herein.

In another example, the following method may be used to generate candidate nucleic acid agents including non-natural nucleic acids: 1) generating particles having immobilized thereon double-stranded nucleic acid agents; 2) removing part of the double-stranded nucleic acid agents to obtain partially single-stranded nucleic acid agents; 3) incorporating modified nucleotides to generate nucleic acid agents comprising modified nucleotides.

In the present application, the screening composition may be a composition comprising at least a target moiety and at least a reference moiety. The screening composition may comprise two or more different target moieties and/or two or more different reference moieties. The target moiety may be a protein (e.g., an antibody), a polynucleotide, a polypeptide, a virus, a microorganism, a small molecule, a whole cell, a cellular component, a liposome, or a combination thereof. For example, the target moiety may include small molecules (e.g., organic dyes), amino acids, carbohydrates, lipids, aminoglycosides, antibiotics, peptides, proteins, post-translational modification, nucleic acids, virus, whole cells and/or cellular components. Small molecule targets of interest generally may have a molecular weight of about 800 Daltons or less. In some embodiments, the target moiety is a protein or a polypeptide moiety. For example, the target moiety may include Tumor Necrosis Factor α, Neutrophil Gelatinase-Associated Lipocalin, Histidine-Rich Protein 2, Platelet-Derived Growth Factors, Vascular Endothelial Growth Factors, Angiopoietins, Complement proteins and Integrins. In some embodiments, the target moiety comprises Tumor Necrosis Factor α, Neutrophil Gelatinase-Associated Lipocalin (NGAL) and/or Histidine-Rich Protein 2 (HRP-2).

In any aspect of the present application, the reference moiety may comprise one or more molecules or may comprise a mixture including a plurality of different molecules. The reference moiety may compete with the target moiety to interact with (e.g., bind to) the candidate nucleic acid agents. In some embodiments, the reference moiety comprises a mixture of proteins, glycans and/or small molecules. For example, the reference moiety may comprise a mixture of blood, plasma, serum, liquid humor, vitreous, urine, tissue fluid, spit, and/or saliva. The blood, plasma, serum, liquid humor, vitreous, urine, tissue fluid, spit, and/or saliva may be from a human being. In some embodiments, the reference moiety is a protein or a polypeptide moiety, such as serum proteins.

In some embodiments, the reference moiety comprises one or more molecules homologous to the target moiety. For example, the one or more molecules may have a homology of at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% to the target molecule. For example, the homology may be from about 25% to about 99%, from about 30% to about 99%, from about 35% to about 99%, from about 40% to about 99%, from about 45% to about 99%, from about 50% to about 99%, from about 55% to about 99%, from about 60% to about 99%, from about 65% to about 99%, from about 70% to about 99%, from about 75% to about 99%, from about 80% to about 99%, from about 85% to about 99%, from about 90% to about 99%, from about 95% to about 99%, or higher.

In any aspect of the present disclosure, the desired property of a selected candidate nucleic acid agent may be an ability to specifically bind to a target moiety with high affinity. The affinity of a candidate nucleic acid agent to bind to a target may be evaluated by measuring an equilibrium dissociation constant for binding the target ($K_{DT}$). A candidate nucleic acid agent with the desired property may bind to a target with a $K_{DT}$ from about 1 fM to about 1 μM (e.g., at least about 500 nM, at least about 100 nM, at least about 50 nM, at least about 10 nM, at least about 8 nM, at least about 6 nM, at least about 4 nM, at least about 2 nM, at least about 1 nM, at least about 900 pM, at least about 800 pM, at least about 700 pM, at least about 600 pM, at least about 500 pM, at least about 400 pM, at least about 300 pM, at least about 200 pM, at least about 100 pM, at least about 90 pM, at least about 80 pM, at least about 70 pM, at least about 60 pM, at least about 50 pM, at least about 40 pM, at least about 30 pM, at least about 20 pM, at least about 10 pM, at least about 5 pM, at least about 1 pM, at least about 500 fM, at least about 100 fM, at least about 50 fM, at least about 10 fM, at least about 5 fM, at least about 1 fM, or greater).

A candidate nucleic acid agent may bind to a reference moiety with an equilibrium dissociation constant $K_{DR}$, and the specificity of a candidate nucleic acid agent to bind to a target may be evaluated with a ratio between $K_{DR}$ and $K_{DT}$. The ratio between the $K_{DR}$ and the $K_{DT}$ may be from about $10^2$ to $10^{12}$, e.g., from about $10^3$ to $10^{12}$, from about $10^4$ to $10^{12}$, from about $10^5$ to $10^{12}$, from about $10^6$ to $10^{12}$, from about $10^7$ to $10^{12}$, from about $10^8$ to $10^{12}$, from about $10^9$ to $10^{12}$, from about $10^{10}$ to $10^{12}$, from about $10^{11}$ to $10^{12}$.

According to any aspect of the present disclosure, the one or more nucleic acid agents identified as having a desired property may bind to the target moiety with a first apparent $K_{DT}$ when the binding occurs in a composition comprising the target moiety but not the reference moiety, and the one or more nucleic acid agents identified as having the desired property may bind to the target moiety with a second apparent $K_{DT}$ when the binding occurs in a composition comprising both the target moiety and the reference moiety, and a difference between the first apparent $K_{DT}$ and the second apparent $K_{DT}$ may be less than about 20% of the value of the first apparent $K_{DT}$. For example, the difference between the first apparent $K_{DT}$ and the second apparent $K_{DT}$ may be less than about 18% of the value of the first apparent $K_{DT}$, less than about 16% of the value of the first apparent $K_{DT}$, less than about 15% of the value of the first apparent $K_{DT}$, less than about 14% of the value of the first apparent $K_{DT}$, less than about 13% of the value of the first apparent $K_{DT}$, less than about 12% of the value of the first apparent $K_{DT}$, less than about 11% of the value of the first apparent $K_{DT}$, less than about 10% of the value of the first apparent $K_{DT}$, less than about 9% of the value of the first apparent $K_{DT}$, less than about 8% of the value of the first apparent $K_{DT}$, less than about 7% of the value of the first apparent $K_{DT}$, less than about 6% of the value of the first apparent $K_{DT}$, less than about 5% of the value of the first apparent $K_{DT}$, less than about 4% of the value of the first apparent $K_{DT}$, less than about 3% of the value of the first apparent $K_{DT}$, less than about 2% of the value of the first apparent $K_{DT}$, less than about 1% of the value of the first apparent $K_{DT}$, less than about 0.5% of the value of the first apparent $K_{DT}$, or less than about 0.1% of the value of the first apparent $K_{DT}$.

According to any aspect of the present disclosure, the first signal may represent an interaction of the candidate nucleic acid agents with the target moiety. For example, the target moiety may be labeled with a first labeling moiety providing a first signal, and an intensity of the first signal may reflect a degree of interaction between the candidate nucleic acid agent and the target moiety. In some embodiments, the interaction between the candidate nucleic acid agent and the target moiety is a binding activity, and a higher intensity of the first signal represents a stronger binding between the candidate nucleic acid agent and the target moiety. The first signal is a fluorescence signal (e.g., a green fluorescence).

According to any aspect of the present disclosure, the second signal may represent an interaction of the candidate nucleic acid agents with the reference moiety. For example, the reference moiety may be labeled with a second labeling moiety providing a second signal, and an intensity of the second signal may reflect a degree of interaction between the candidate nucleic acid agent and the reference moiety. In some embodiments, the interaction between the candidate nucleic acid agent and the reference moiety is a binding activity, and a lower intensity of the second signal represents a weaker binding between the candidate nucleic acid agent and the reference moiety, which in turn indicates a higher specificity. In some embodiments, the second signal is a fluorescence signal (e.g., a red fluorescence).

In some embodiments, the first and/or the second labeling moiety is added (e.g., attached or conjugated) to the target and/or the reference moiety before their binding to the candidate nucleic acid agents, respectively. In some cases, the first and/or the second labeling moiety may be added to a complex formed between the target or the reference moiety and the candidate nucleic acid agents subsequent to the interaction of the target or the reference moiety with the candidate nucleic acid agents.

According to any aspect of the present disclosure, the sorting parameter may represent a parameter useful for identifying particles with candidate nucleic acid agents having the desired property immobilized thereon. The sorting parameter of a particle may comprise quantified value(s) reflecting a property of the candidate nucleic acid agents immobilized on the particle. For example, the sorting parameter may comprise a first value indicating quantified intensity of a first signal and a second value indicating quantified intensity of a second signal. The intensity of the first signal may reflect the strength of the interaction between the candidate nucleic acid agents and the target moiety. The intensity of the second signal may reflect the strength of the interaction between the candidate nucleic acid agents and the reference moiety.

In the present application, the sorting range may be determined with at least one threshold value. By comparing the value of a sorting parameter with the at least one threshold, the sorting parameter may be determined as falling in or out of the sorting range. In some embodiments, the sorting range comprises a first threshold and a second threshold, and the sorting parameter of a particular particle is considered as falling in the sorting range when the intensity of the first signal of the particular particle is above the first threshold and the intensity of the second signal of the particular particle is below the second threshold.

The first threshold may be determined by a process comprising: exposing the plurality of particles with the mixture of candidate nucleic acid agents immobilized thereon to a first prescreening composition comprising a saturating concentration of the target moiety, and determining a maximum mean intensity of a signal indicating an interaction of the candidate nucleic acid agents with the target moiety in the first prescreening composition, and the first prescreening composition does not comprise the reference moiety. The first threshold may be set to be at least 30% (e.g., at least 35%, at least 40%, at least 45%, at least 50%, at least 55%, at least 60%, at least 65%, at least 70%, at least 75%, at least 80%, at least 85% or more) of the maximum mean intensity of the signal indicating an interaction of the candidate nucleic acid agents with the target moiety in the first prescreening composition.

The second threshold may be determined by a process comprising exposing the plurality of particles with the mixture of candidate nucleic acid agents immobilized thereon to a second prescreening composition comprising a saturating concentration of the reference moiety, and determining a maximum mean intensity of a signal indicating an interaction of the candidate nucleic acid agents with the reference moiety in the second prescreening composition, and the second prescreening composition does not comprise the target moiety. The second threshold may be set to be at most 20% (e.g., at most 18%, at most 16%, at most 15%, at most 14%, at most 13%, at most 12%, at most 11%, at most 10%, at most 9%, at most 8%, at most 7%, at most 6%, at most 5%, at most 4%, at most 3%, at most 2%, or at most 1%) of the maximum mean intensity of the signal indicating an interaction of the candidate nucleic acid agents with the reference moiety in the second prescreening composition.

The concentration of the target moiety and the concentration of the reference moiety may be independently adjusted to enable the sorting parameter of about 0.05% to about 1% of the plurality of particles screened to be within the predetermined sorting range. As discussed above, for example, by changing the concentration of the target moiety and/or the reference moiety in the screening composition, the percentage of particles having a sorting parameter within the predetermined soring range may vary accordingly, and when about 0.05% to about 1% (e.g., about 0.05% to about 0.08%, about 0.05% to about 0.1%, about 0.05% to about 0.12%, about 0.05% to about 0.15%, about 0.05% to about 0.2%, about 0.05% to about 0.25%, about 0.05% to about 0.3%, about 0.05% to about 0.35%, about 0.05% to about 0.4%, about 0.05% to about 0.45%, about 0.05% to about 0.5%, about 0.05% to about 0.55%, about 0.05% to about 0.6%, about 0.05% to about 0.65%, about 0.05% to about 0.7%, about 0.05% to about 0.75%, about 0.05% to about 0.8%, about 0.05% to about 0.85%, about 0.05% to about 0.9%, about 0.05% to about 0.95%, etc.) of the particles have a sorting parameter within the predetermined soring range, the concentration of the target moiety and that of the reference moiety in the screening composition are considered as appropriate.

The first labeling moiety and the second labeling moiety may be independently selected from the following agents or an antibody comprising one or more of the following agents: radioactive isotopes, fluorescers, chemiluminescers, chromophores, enzymes, enzyme substrates, enzyme cofactors, enzyme inhibitors, dyes, metal ions, metal sols, ligands (e.g., biotin, avidin, streptavidin or haptens), affinity tags, etc. For example, an affinity tag may include a monocytic adaptor protein (MONA) binding peptide, a T7 binding peptide, a streptavidin binding peptide, a polyhistidine tract, protein A (Nilsson et al., EMBO J. 4:1075 (1985); Nilsson et al., Methods Enzymol. 198:3 (1991)), glutathione S transferase (Smith and Johnson, Gene 67:31 (1988)), Glu-Glu affinity tag (Grussenmeyer et al., Proc. Natl. Acad. Sci. USA 82:7952 (1985)), substance P, FLAG peptide (Hopp et al., Biotechnology 6:1204 (1988)), or other antigenic epitope or binding domain. See, in general, Ford et al., Protein Expression and Purification 2:95 (1991). DNA molecules encoding affinity tags are available from commercial suppliers (e.g., Pharmacia Biotech, Piscataway, N.J.).

Any fluorescent label may be suitable for the use as the first labeling moiety or the second labeling moiety, or for being comprised by the first labeling moiety or the second labeling moiety. A suitable fluorescent polypeptide will be one that will readily provide a detectable signal that can be assessed qualitatively (positive/negative) and quantitatively (comparative degree of fluorescence). Exemplary fluorescent polypeptides include, but are not limited to, yellow fluorescent protein (YFP), cyan fluorescent protein (CFP), GFP, mRFP, RFP (tdimer2), HCRED, etc., or any mutant (e.g., fluorescent proteins modified to provide for enhanced fluorescence or a shifted emission spectrum), analog, or derivative thereof.

Biotin-based labels may also be used in the present application. Suitable biotinylation agents may include amine-reactive and thiol-reactive agents. For the biotinylation of proteins, nucleic acids, carbohydrates, carboxylic acids, see, e.g., chapter 4, Molecular Probes Catalog, Haugland, 6th Ed. 1996, hereby incorporated by reference. A biotinylated substrate can be detected by binding of a detectably labeled biotin binding partner, such as avidin or streptavidin.

For example, the first labeling moiety and the second labeling moiety may be independently chosen from the following agents or an antibody comprising any of the following agents: a biotin, an avidin, a streptavidin and a hapten; or, may be independently chosen from a group consisting of an acridine dye, a cyanine dye, a fluorone dye, an oxazine dye, a phenanthridine dye, and a rhodamine dye.

For example, the first labeling moiety and the second labeling moiety may be independently chosen from the following agents or an antibody comprising any of the following agents: AlexaFluor350, AlexaFluor488, AlexaFluor647, AlexaFluor405, AlexaFluor430, AlexaFluor500, AlexaFluor514, AlexaFluor532, AlexaFluor546, AlexaFluor555, AlexaFluor568, AlexaFluor594, AlexaFluor610, AlexaFluor633, AlexaFluor635, AlexaFluor660, AlexaFluor680, AlexaFluor700, AlexaFluor750, and AlexaFluor790.

In some embodiments, the first labeling moiety is a fluoresce reagent AlexaFluor-488 (green) or an antibody comprising AlexaFluor-488, and the second labeling moiety is a fluoresce reagent AlexaFluor-647 (red) or an antibody comprising AlexaFluor-647.

According to any aspect of the present disclosure, the concentration of the target moiety in the screening composition may be from about 0.001 nM to about 1 µM, e.g., from about 0.01 nM to about 1 µM, from about 0.1 nM to about 1 µM, from about 0.5 nM to about 1 µM, from about 1 nM to about 1 µM, from about 5 nM to about 1 µM, from about 10 nM to about 1 µM, from about 50 nM to about 1 µM, from about 100 nM to about 1 µM, from about 200 nM to about 1 µM, from about 300 nM to about 1 µM, from about 400 nM to about 1 µM, from about 500 nM to about 1 µM, from about 600 nM to about 1 µM, from about 700 nM to about 1 µM, from about 800 nM to about 1 µM, or from about 900 nM to about 1 µM.

According to any aspect of the present disclosure, the concentration of the reference moiety in the screening composition may be from about 1 nM to about 1 mM, e.g., from about 50 nM to about 1 mM, from about 100 nM to about 1 mM, from about 200 nM to about 1 mM, from about 300 nM to about 1 mM, from about 400 nM to about 1 mM, from about 500 nM to about 1 mM, from about 600 nM to about 1 mM, from about 700 nM to about 1 mM, from about 800 nM to about 1 mM, from about 900 nM to about 1 mM, from about 1 µM to about 1 mM, from about 50 µM to about 1 mM, from about 100 µM to about 1 mM, from about 200 µM to about 1 mM, from about 300 µM to about 1 mM, from about 400 µM to about 1 mM, from about 500 µM to about 1 mM, from about 600 µM to about 1 mM, from about 700 µM to about 1 mM, from about 800 µM to about 1 mM, or from about 900 µM to about 1 mM.

A ratio between the concentration of the target moiety and the concentration of the reference moiety in the screening composition may be from about $1:10^9$ to about 1:1, e.g., from about $1:10^8$ to about 1:1, from about $1:10^7$ to about 1:1, from about $1:10^6$ to about 1:1, from about $1:10^5$ to about 1:1, from about $1:10^4$ to about 1:1, from about $1:10^3$ to about 1:1, from about $1:10^2$ to about 1:1, or from about 1:10 to about 1:1.

Isolation and/or sorting may be conducted using a variety of methods and/or devices known by those skilled in the art, such as flow cytometry (e.g., Fluorescence Activated Cell Sorting (FACS) or Ramen flow cytometry), fluorescence microscopy, optical tweezers, micro-pipettes, and microfluidic magnetic separation devices and methods. In some embodiments, where the labeling moiety comprises a fluorescent label, Fluorescence Activated Cell Sorting (FACS) may be employed to quantitatively sort particles immobilized nucleic acid agents based on one or more fluorescence signals.

In some embodiments, before immobilizing the mixture of candidate nucleic acid agents onto a plurality of particles, the candidate nucleic acid agents are pre-enriched to reduce the time required for identifying the nucleic acid agents having a desired property. This may be conducted with a pre-enriching composition. The pre-enriching composition may comprise the target moiety, and upon incubating the mixture of candidate nucleic acid agents with the pre-enriching composition, a pre-enriched pool of candidate nucleic acid agents may be obtained to be immobilized onto the plurality of particles. The pre-enriched pool may have decreased sequence diversity relative to the mixture of candidate nucleic acid agents prior to pre-enriching. The pre-enriching may be conducted using bead-based selection, wherein the target moiety in the pre-enriching composition may be immobilized on a plurality of beads.

In some embodiments, a method or a kit according to the present disclosure may further comprise an operation or a component for generating an enriched mixture of candidate nucleic acid agents from the selected particle. The operation or component for generating an enriched mixture of candidate nucleic acid agents may utilize nucleic acid amplification, such as e.g., PCR, reverse transcriptase PCR or primer extension as appropriate in view of the candidate nucleic acid agent sequences being amplified.

A kit according to the present disclosure may comprise devices and/or agents for conducting nucleic acid amplification (e.g., in the component for identifying the one or more nucleic acid agents having the desired property from the selected particles, and/or in the component for generating an enriched mixture of candidate nucleic acid agents. The devices and/or agents for conducting nucleic acid amplification may comprise suitable buffers, dNTPs, polymerases, and other agents necessary for nucleic acid amplification. Any suitable polymerase may be used, for example, a polymerase may be selected from Bst 3.0 DNA Polymerase, Bst 2.0 DNA Polymerase, Therminator™ DNA Polymerase, Deep VentR™ DNA Polymerase, Deep VentR™ (exo-) DNA Polymerase, OneTaq® Hot Start DNA Polymerase, Sulfolobus DNA Polymerase IV, phi29 DNA Polymerase, Klenow Fragment (3'→5' exo-), DNA Polymerase I, Large (Klenow) Fragment, KOD Hot Start DNA Polymerase, KOD Xtreme™ Hot Start DNA Polymerase, or a combination thereof.

In some embodiments, the immobilizing the mixture of candidate nucleic acid agents onto a plurality of particles, exposing the plurality of particles to a screening composition, isolating from the plurality of particles one or more selected particles, and generating an enriched mixture of candidate nucleic acid agents may constitute a first round of screening. The method may include one or more additional rounds of screening, e.g., two, three, four or more additional rounds of screening, wherein the enriched mixture of candidate nucleic acid agents obtained from one round of screening may be used as the mixture of candidate nucleic acid agents to be immobilized onto the plurality of particles in the next round of screening. For example, following a first round of screening in which $1\times10^7$ to $1\times10^8$ particles (i.e., $1\times10^7$ to $1\times10^8$ unique sequences) were screened, an enriched particle pool may be provided which has about $1\times10^5$ to $1\times10^6$ particles, which particles include from about 100 to about 1000 particles with a unique sequence thereon.

In some embodiments, to identify one or more nucleic acid agents having a desired property from a mixture of candidate nucleic acid agents, a concentration of the target moiety and a concentration of the reference moiety in the screening composition may be determined as described in the present disclosure, and then, one or more rounds of screening may be performed with only one signal indicating an interaction of the candidate nucleic acid agents with the target moiety or with the reference moiety in the screening composition. For example, in the one or more rounds of screening, only the target moiety or the reference moiety in the screening composition is labeled with a labeling moiety.

In some embodiments, the screening composition may comprise two or more different target moieties and/or two or more different reference moieties. To identify one or more nucleic acid agents having a desired property from a mixture of candidate nucleic acid agents, a concentration of each of the two or more different target moieties and a concentration of each of the two or more different reference moieties in the screening composition may be determined as described in the present disclosure, and then, one or more rounds of screening may be performed with multiple (e.g., three or more, such as four, five, six, seven or more) different signals indicating an interaction of the candidate nucleic acid agents with each of the two or more different target moieties or with each of the two or more reference moieties in the screening composition. For example, in the one or more rounds of screening, each of the two or more target moieties and each of the two or more reference moieties in the screening composition is labeled with a unique and distinct labeling moiety.

The present disclosure also provides isolated nucleic acid agents identified using the methods and kits disclosed herein, the isolated nucleic acid agents specifically binds to a corresponding target moiety with high affinity.

In some embodiments, the isolated nucleic acid agent specifically binds to Tumor Necrosis Factor α or a part thereof, and comprises a sequence as set forth in SEQ ID NO: 1.

In some embodiments, the isolated nucleic acid agent specifically binds to Neutrophil Gelatinase-Associated Lipocalin or a part thereof, which comprises a sequence as set forth in SEQ ID NO: 3.

In some embodiments, the isolated nucleic acid agent specifically binds to Histidine-Rich Protein 2 or a part thereof, which comprises a sequence as set forth in SEQ ID NO: 4.

The present disclosure also provides the following embodiments:

1. A method for identifying one or more nucleic acid agents having a desired property from a mixture of candidate nucleic acid agents, wherein the mixture of candidate nucleic acid agents comprises a plurality of single stranded nucleic acids, the method comprising:
a) providing a plurality of particles with said candidate nucleic acid agents immobilized thereon, wherein each of said plurality of particles comprises at most a subset of said candidate nucleic acid agents within said mixture; optionally, operation a) further comprises immobilizing the mixture of candidate nucleic acid agents onto the plurality of particles, wherein each of the plurality of particles comprises at most a subset of the candidate nucleic acid agents;
b) exposing said plurality of particles with said candidate nucleic acid agents immobilized thereon to a screening composition comprising a target moiety and a reference moiety, wherein an interaction of said candidate nucleic acid agents with the target moiety is indicated by a first signal, an interaction of said candidate nucleic acid agents with the reference moiety is indicated by a second signal, and an intensity of said first signal together with an intensity of said second signal for a particular particle provide a sorting parameter of the particular particle, wherein a concentration of the target moiety and a concentration of the reference moiety are respectively set at a value enabling the sorting parameter of about 0.05% to about 1% of the plurality of particles to be within a predetermined sorting range;
c) isolating from said plurality of particles one or more selected particles having a sorting parameter within said predetermined sorting range, wherein the one or more selected particles comprises said one or more nucleic acid agents having the desired property; and
d) identifying the one or more nucleic acid agents having the desired property from the one or more selected particles.

2. The method according to embodiment 1, wherein said sorting range is determined with a first threshold and a second threshold, and the sorting parameter of a particular particle is within said sorting range when the intensity of the first signal of the particular particle is above said first threshold and the intensity of the second signal of the particular particle is below said second threshold.

3. The method according to embodiment 2, wherein said first threshold is determined by a process comprising:
exposing the plurality of particles with the mixture of candidate nucleic acid agents immobilized thereon to a first prescreening composition comprising a saturating concentration of the target moiety, and
determining a maximum mean intensity of a signal indicating an interaction of said candidate nucleic acid agents with the target moiety in said first prescreening composition,
wherein said first prescreening composition does not comprise the reference moiety.

4. The method according to embodiment 3, wherein said first threshold is set to be at least one half of said maximum mean intensity of the signal indicating an interaction of said candidate nucleic acid agents with the target moiety in said first prescreening composition.

5. The method according to any of embodiments 2-4, wherein said second threshold is determined by a process comprising:
exposing the plurality of particles with the mixture of candidate nucleic acid agents immobilized thereon to a second prescreening composition comprising a saturating concentration of the reference moiety, and
determining a maximum mean intensity of a signal indicating an interaction of said candidate nucleic acid agents with the reference moiety in said second prescreening composition,
wherein said second prescreening composition does not comprise the target moiety.

6. The method according to embodiment 5, wherein said second threshold is set to be at most one tenth of the maximum mean intensity of the signal indicating an interaction of said candidate nucleic acid agents with the reference moiety in said second prescreening composition.

7. The method according to any of embodiments 1-6, wherein a ratio between the concentration of the target moiety and the concentration of the reference moiety in the screening composition is from about $1:10^9$ to about 1:1.

8. The method according to any of embodiments 1-7, wherein the concentration of the target moiety in the screening composition is from about 0.001 nM to about 1 µM.

9. The method according to any of embodiments 1-8, wherein the concentration of the reference moiety in the screening composition is from about 1 nM to about 1 mM.

10. The method according to any of embodiments 1-9, wherein each of the plurality of particles comprises multiple copies of a single candidate nucleic acid agent immobilized thereon, and wherein the candidate nucleic acid agent immobilized on any one particle of the plurality of particles is different from that immobilized on at least one other particle of the plurality of particles.

11. The method according to any of embodiments 1-10, wherein said target moiety is labeled with a first labeling moiety, and said reference moiety is labeled with a second labeling moiety different from said first labeling moiety.

12. The method according to embodiment 11, wherein the interaction of said candidate nucleic acid agents with the target moiety is a binding interaction, which is indicated by a signal generated from said first labeling moiety of said target moiety.

13. The method according to any of embodiments 11-12, wherein the interaction of said candidate nucleic acid agents with the reference moiety is a binding interaction, which is indicated by a signal generated from said second labeling moiety of said reference moiety.

14. The method according to any of embodiments 11-13, wherein said first labeling moiety and said second labeling moiety are independently selected from the following agents or an antibody comprising one or more of the following agents: a radioactive isotope, a fluorescer, a chemiluminescer, a chromophore, an enzyme, an enzyme substrate, an enzyme cofactor, an enzyme inhibitor, a dye, a metal ion, a metal sol, a ligand, and an affinity tag.

15. The method according to embodiment 14, wherein said first labeling moiety and said second labeling moiety are independently selected from the following agents or an antibody comprising one or more of the following agents: a biotin, an avidin, a streptavidin and a hapten.

16. The method according to embodiment 14, wherein said first labeling moiety and said second labeling moiety are independently selected from the following agents or an antibody comprising one or more of the following agents: an acridine dye, a cyanine dye, a fluorone dye, an oxazine dye, a phenanthridine dye, and a rhodamine dye.

17. The method according to embodiment 14, wherein said first labeling moiety and said second labeling moiety are independently selected from the following agents or an antibody comprising one or more of the following agents: AlexaFluor350, AlexaFluor488, AlexaFluor647, AlexaFluor405, AlexaFluor430, AlexaFluor500, AlexaFluor514, AlexaFluor532, AlexaFluor546, AlexaFluor555, AlexaFluor568, AlexaFluor594, AlexaFluor610, AlexaFluor633, AlexaFluor635, AlexaFluor660, AlexaFluor680, AlexaFluor700, AlexaFluor750, and AlexaFluor790.

18. The method according to any of embodiments 1-17, wherein the target moiety is a protein or a polypeptide moiety.

19. The method according to any of embodiments 1-18, wherein the reference moiety is a protein or a polypeptide moiety.

20. The method according to embodiment 19, wherein the reference moiety comprises serum proteins.

21. The method according to any of embodiments 1-20, wherein the single stranded nucleic acid agent is selected from a DNA molecule, a RNA molecule, a chemically modified DNA molecule, and a chemically modified RNA molecule.

22. The method according to embodiment 21, wherein the single stranded nucleic acid agent is a DNA molecule.

23. The method according to any of embodiments 1-22, wherein the single stranded nucleic acid agent comprises one or more non-natural nucleic acid.

24. The method according to any of embodiments 1-23, wherein one or more of the single stranded nucleic acid agents comprises a molecule conjugated thereto.

25. The method according to embodiment 24, wherein the molecule conjugated to one or more of the single stranded nucleic acids is a small molecule, a fluorophore, a peptide, and/or an siRNA.

26. The method according to any of embodiments 1-25, wherein said desired property is an ability to specifically bind to a target or an activity induced by such specific binding.

27. The method according to embodiment 26, wherein the activity induced by such specific binding is a catalytic activity, a modified catalytic activity, an inhibition activity, an activation activity, a modification of an inhibition activity, an activation activity, a structure switching activity, a modification of a structure switching activity, and/or a cooperative activity.

28. The method according to any of embodiments 1-27, wherein said particle is non-magnetic, magnetic or paramagnetic.

29. The method according to any of embodiments 1-28, wherein each of said plurality of particles has at least one dimension of from about 50 nm to about 100 µm.

30. The method according to any of embodiments 1-29, wherein said plurality of particles comprise carboxylic acid paramagnetic particles having an average diameter of about 1 µm.

31. The method according to any of embodiments 1-30, wherein the plurality of particles comprises from about $1\times10^2$ to about $1\times10^{14}$ particles.

32. The method according to any of embodiments 1-31, wherein each particle of the plurality of particles comprises from about $1\times10^2$ to about $1\times10^{10}$ candidate nucleic acid agents bound thereto.

33. The method according to any of embodiments 1-32, wherein each of the candidate nucleic acid agents is coupled to a particle of the plurality of particles via a linker.

34. The method according to embodiment 33, wherein the linker is a cleavable linker, a non-cleavable linker or a combination thereof.

35. The method according to any of embodiments 33-34, wherein the linker is an amino-modified nucleic acid primer.

36. The method according to any of embodiments 1-35, wherein said isolating from said plurality of particles one or more selected particles comprises sorting the plurality of particles using flow cytometry, fluorescence microscopy, an optical tweezer, a micro-pipette, and/or microfluidic magnetic separation.

37. The method according to embodiment 36, wherein the flow cytometry is fluorescence activated cell sorting (FACS) or Ramen flow cytometry.

38. The method according to any of embodiments 2-37, wherein said first signal and said second signal are fluorescent signal, and wherein said first threshold and said second threshold are fluorescence intensity threshold level.

39. The method according to any of embodiments 1-38, wherein the method further comprises, prior to immobilizing the mixture of candidate nucleic acid agents onto a plurality of particles, pre-enriching the candidate nucleic acid agents to obtain a pre-enriched pool of candidate nucleic acid agents to be immobilized on to the plurality of particles, wherein the pre-enriched pool has decreased sequence diversity relative to the mixture of candidate nucleic acid agents prior to pre-enriching.

40. The method according to embodiment 39, wherein said pre-enriching comprises incubating said mixture of candidate nucleic acid agents with a pre-enriching composition comprising the target moiety to facilitate interactions between the candidate nucleic acid agents and the target moiety, and identifying candidate nucleic acid agents capable of interacting with said target moiety.

41. The method according to embodiment 40, wherein the target moiety in the pre-enriching composition is immobilized on a bead.

42. The method according to any of embodiments 1-41, further comprising preparing the mixture of candidate nucleic acid agents by a method comprising generating a library of single stranded nucleic acids, wherein each single stranded nucleic acid in the library comprises a region of randomized sequence.

43. The method according to any of embodiments 1-42, wherein the single stranded nucleic acid agent is an aptamer.

44. The method according to any of embodiments 1-43, further comprising c2) generating an enriched mixture of candidate nucleic acid agents from the selected particle prior to the operation d).

45. The method according to embodiment 44, wherein operations a), b), c), and c2) constitute one round of screening, and the method comprises two or more said rounds of screening, wherein the enriched mixture of candidate nucleic acid agents obtained from operation c2) of one round of screening is used as the mixture of candidate nucleic acid agents to be immobilized onto the plurality of particles in operation a) of the next round of screening.

46. The method according to any of embodiments 1-45, wherein the one or more nucleic acid agents identified as having a desired property binds to the target moiety with a $K_{DT}$ of from about 1 fM to about 1 µM.

47. The method according to any of embodiments 1-46, wherein the one or more nucleic acid agents identified as having a desired property binds to the target moiety with a $K_{DT}$ and binds to the reference moiety with a $K_{DR}$, and a ratio between the $K_{DR}$ and the $K_{DT}$ is from about $10^2$ to $10^{12}$.

48. The method according to any of embodiments 1-47, wherein the one or more nucleic acid agents identified as having a desired property binds to the target moiety with a first apparent $K_{DT}$ when the binding occurs in a composition comprising said target moiety but not said reference moiety, and the one or more nucleic acid agents identified as having the desired property binds to the target moiety with a second apparent $K_{DT}$ when the binding occurs in a composition comprising both said target moiety and said reference moiety, and wherein a difference between said first apparent $K_{DT}$ and said second apparent $K_{DT}$ is less than about 20% of the value of the first apparent $K_{DT}$.

49. The method according to any of embodiments 44-48, wherein the enriched mixture of candidate nucleic acid agents is generated by a method comprising nucleic acid amplification.

50. The method according to embodiment 49, wherein said nucleic acid amplification comprises PCR or reverse transcriptase PCR.

51. The method according to any of embodiments 1-50, wherein in the operation a), the mixture of candidate nucleic acid agents is immobilized onto the plurality of particles by a method comprising emulsion PCR.

52. The method according to any of embodiments 1-51, wherein the target moiety comprises a protein or a part thereof selected from the group consisting of Tumor Necrosis Factor α, Neutrophil Gelatinase-Associated Lipocalin, Histidine-Rich Protein 2, Platelet-Derived Growth Factors, Vascular Endothelial Growth Factors, Angiopoietins, Complement proteins and Integrins.

53. The method according to any of embodiments 1-52, wherein the reference moiety comprises one or more molecules homologous to the target moiety.

54. The method according to any of embodiments 53, wherein the one or more molecules have a homology of 50%~99% to the target moiety.

55. The method according to any of embodiments 1-54, wherein the reference moiety comprises a mixture comprising proteins, glycans and/or small molecules.

56. The method according to any of embodiments 1-55, wherein the reference moiety comprises a mixture comprising blood, plasma, serum, liquid humor, vitreous, urine, tissue fluid, spit, and/or saliva.

57. The method according to embodiment 56, wherein the blood, plasma, serum, liquid humor, vitreous, urine, tissue fluid, spit, and/or saliva is from a human being.

58. A nucleic acid agent specifically binding to Tumor Necrosis Factor α or a part thereof, which comprises a sequence as set forth in SEQ ID NO: 1.

59. A nucleic acid agent specifically binding to Neutrophil Gelatinase-Associated Lipocalin or a part thereof, which comprises a sequence as set forth in SEQ ID NO: 3.

60. A nucleic acid agent specifically binding to Histidine-Rich Protein 2 or a part thereof, which comprises a sequence as set forth in SEQ ID NO: 4.

61. A kit for identifying one or more nucleic acid agents having a desired property from a mixture of candidate nucleic acid agents, wherein the mixture of candidate nucleic acid agents comprises a plurality of single stranded nucleic acids, and the kit comprises:
a plurality of particles;
a mixture of candidate nucleic acid agents immobilized or to be immobilized onto the plurality of particles; and
a screening composition for screening the plurality of particles with the mixture of candidate nucleic acid agents immobilized thereon, wherein the screening composition comprises a target moiety and a reference moiety, a concentration of the target moiety and a concentration of the reference moiety in the screening composition are adjustable to enable sorting out of selected particles with the one or more nucleic acid agents having the desired property immobilized thereon;
wherein a percentage of the selected particles is about 0.05% to about 1% of the plurality of particles screened.

62. The kit according to embodiment 61, wherein said screening comprises exposing the plurality of particles with the mixture of candidate nucleic acid agents immobilized thereon to the screening composition, wherein an interaction of said candidate nucleic acid agents with the target moiety is indicated by a first signal, an interaction of said candidate nucleic acid agents with the reference moiety is indicated by a second signal, and an intensity of said first signal together with an intensity of said second signal for a particular particle provide a sorting parameter of the particular particle, and wherein the concentration of the target moiety and the concentration of the reference moiety enable the sorting parameter of about 0.05% to about 1% of the plurality of particles screened to be within a predetermined sorting range.

63. The kit according to any of embodiments 61-62, further comprising a component for isolating said selected particles.

64. The kit according to any of embodiments 61-63, further comprising a component for identifying the one or more nucleic acid agents having the desired property from the selected particles.

65. The kit according to any of embodiments 62-64, wherein said sorting range is determined with a first threshold and a second threshold, and the sorting parameter of a particular particle is within said sorting range when the intensity of the first signal of the particular particle is above said first threshold and the intensity of the second signal of the particular particle is below said second threshold.

66. The kit according to embodiment 65, further comprising a first prescreening composition comprising a saturating concentration of the target moiety while not comprising the reference moiety, wherein said first threshold is determined by a process comprising:
exposing the plurality of particles with the mixture of candidate nucleic acid agents immobilized thereon to the first prescreening composition, and determining a maximum mean intensity of a signal indicating an interaction of said candidate nucleic acid agents with the target moiety in said first prescreening composition.

67. The kit according to embodiment 66, wherein said first threshold is set to be at least one half of said maximum mean intensity of the signal indicating an interaction of said candidate nucleic acid agents with the target moiety in said first prescreening composition.

68. The kit according to any of embodiments 65-67, further comprising a second prescreening composition comprising a saturating concentration of the reference moiety while not comprising the target moiety, wherein said second threshold is determined by a process comprising: exposing the plurality of particles with the mixture of candidate nucleic acid agents immobilized thereon to the second prescreening composition, and determining a maximum mean intensity of a signal indicating an interaction of said candidate nucleic acid agents with the reference moiety in said second prescreening composition.

69. The kit according to embodiment 68, wherein said second threshold is set to be at most one tenth of the maximum mean intensity of the signal indicating an interaction of said candidate nucleic acid agents with the reference moiety in said second prescreening composition.

70. The kit according to any of embodiments 61-69, wherein a ratio between the concentration of the target moiety and the concentration of the reference moiety in the screening composition is from about $1:10^9$ to about $1:1$.

71. The kit according to any of embodiments 61-70, wherein the concentration of the target moiety in the screening composition is from about 0.001 nM to about 1 µM.

72. The kit according to any of embodiments 61-71, wherein the concentration of the reference moiety in the screening composition is from about 1 nM to about 1 mM.

73. The kit according to any of embodiments 61-72, wherein after immobilizing the mixture of candidate nucleic acid agents onto the plurality of particles, each of the plurality of particles comprises multiple copies of a single candidate nucleic acid agent immobilized thereon, and wherein the candidate nucleic acid agent immobilized on any one particle of the plurality of particles is different from that immobilized on at least one other particle of the plurality of particles.

74. The kit according to any of embodiments 62-73, wherein said target moiety is labeled with a first labeling moiety, and said reference moiety is labeled with a second labeling moiety different from said first labeling moiety.

75. The kit according to embodiment 74, wherein the interaction of said candidate nucleic acid agents with the target moiety is a binding interaction, which is indicated by a signal generated from said first labeling moiety of said target moiety.

76. The kit according to any of embodiments 74-75, wherein the interaction of said candidate nucleic acid agents with the reference moiety is a binding interaction, which is indicated by a signal generated from said second labeling moiety of said reference moiety.

77. The kit according to any of embodiments 74-76, wherein said first labeling moiety and said second labeling moiety are independently selected from the following agents or an antibody comprising one or more of the following agents: a radioactive isotope, a fluorescer, a chemiluminescer, a chromophore, an enzyme, an enzyme substrate, an enzyme cofactor, an enzyme inhibitor, a dye, a metal ion, a metal sol, a ligand, and an affinity tag.

78. The kit according to embodiment 77, wherein said first labeling moiety and said second labeling moiety are independently selected from the following agents or an antibody comprising one or more of the following agents: a biotin, an avidin, a streptavidin and a hapten.

79. The kit according to embodiment 77, wherein said first labeling moiety and said second labeling moiety are independently selected from the following agents or an antibody comprising one or more of the following agents: an acridine dye, a cyanine dye, a fluorone dye, an oxazine dye, a phenanthridine dye, and a rhodamine dye.

80. The kit according to embodiment 77, wherein said first labeling moiety and said second labeling moiety are independently selected from the following agents or an antibody comprising one or more of the following agents: AlexaFluor350, AlexaFluor488, AlexaFluor647, AlexaFluor405, AlexaFluor430, AlexaFluor500, AlexaFluor514, AlexaFluor532, AlexaFluor546, AlexaFluor555, AlexaFluor568, AlexaFluor594, AlexaFluor610, AlexaFluor633, AlexaFluor635, AlexaFluor660, AlexaFluor680, AlexaFluor700, AlexaFluor750, and AlexaFluor790.

81. The kit according to any of embodiments 61-80, wherein the target moiety is a protein or a polypeptide moiety.

82. The kit according to any of embodiments 61-81, wherein the reference moiety is a protein or a polypeptide moiety.

83. The kit according to embodiment 82, wherein the reference moiety comprises serum proteins.

84. The kit according to any of embodiments 61-83, wherein the single stranded nucleic acid agent is selected from a DNA molecule, a RNA molecule, a chemically modified DNA molecule, and a chemically modified RNA molecule.

85. The kit according to embodiment 84, wherein the single stranded nucleic acid agent is a DNA molecule.

86. The kit according to any of embodiments 61-85, wherein the single stranded nucleic acid agent comprises one or more non-natural nucleic acid.

87. The kit according to any of embodiments 61-86, wherein one or more of the single stranded nucleic acid agents comprises a molecule conjugated thereto.

88. The kit according to embodiment 87, wherein the molecule conjugated to one or more of the single stranded nucleic acids is a small molecule, a fluorophore, a peptide, and/or an siRNA.

89. The kit according to any of embodiments 61-88, wherein said desired property is an ability to specifically bind to a target or an activity induced by such specific binding.

90. The kit according to embodiment 89, wherein the activity induced by such specific binding is a catalytic activity, a modified catalytic activity, an inhibition activity, an activation activity, a modification of an inhibition activity, an activation activity, a structure switching activity, a modification of a structure switching activity, and/or a cooperative activity.

91. The kit according to any of embodiments 61-90, wherein said particle is non-magnetic, magnetic or paramagnetic.

92. The kit according to any of embodiments 61-91, wherein each of said plurality of particles has at least one dimension of from about 50 nm to about 100 µm.

93. The kit according to any of embodiments 61-92, wherein said plurality of particles comprise carboxylic acid paramagnetic particles having an average diameter of about 1 µm.

94. The kit according to any of embodiments 61-93, wherein the plurality of particles comprises from about $1\times10^2$ to about $1\times10^{14}$ particles.

95. The kit according to any of embodiments 61-94, wherein after immobilizing the mixture of the candidate nucleic acid agents onto the plurality of particles, each particle of the plurality of particles comprises from about $1\times10^2$ to about $1\times10^{10}$ candidate nucleic acid agents bound thereto.

96. The kit according to any of embodiments 61-95, wherein each of the candidate nucleic acid agents is coupled to a particle of the plurality of particles via a linker.

97. The kit according to embodiment 96, wherein the linker is a cleavable linker, a non-cleavable linker or a combination thereof.

98. The kit according to any of embodiments 96-97, wherein the linker is an amino-modified nucleic acid primer.

99. The kit according to any of embodiments 63-98, wherein isolating said selected particles comprises using flow cytometry, fluorescence microscopy, an optical tweezer, a micro-pipette, and/or microfluidic magnetic separation.

100. The kit according to embodiment 99, wherein the flow cytometry is fluorescence activated cell sorting (FACS) or Ramen flow cytometry.

101. The kit according to any of embodiments 65-100, wherein said first signal and said second signal are fluorescent signal, and wherein said first threshold and said second threshold are fluorescence intensity threshold level.

102. The kit according to any of embodiments 61-101, further comprising a pre-enriching composition for pre-enriching the candidate nucleic acid agents prior to immobilizing them onto the plurality of particles, wherein the pre-enriching composition comprises the target moiety, and upon incubating said mixture of candidate nucleic acid agents with the pre-enriching composition, a pre-enriched pool of candidate nucleic acid agents is obtained to be immobilized onto said plurality of particles, wherein the pre-enriched pool has decreased sequence diversity relative to the mixture of candidate nucleic acid agents prior to pre-enriching.

103. The kit according to embodiment 102, wherein the target moiety in the pre-enriching composition is immobilized on a bead.

104. The kit according to any of embodiments 61-103, wherein the single stranded nucleic acid agent is an aptamer.

105. The kit according to any of embodiments 61-104, further comprising a component for generating an enriched mixture of candidate nucleic acid agents from the selected particle.

106. The kit according to any of embodiments 61-105, wherein the one or more nucleic acid agents identified as having a desired property binds to the target moiety with a $K_{DT}$ of from about 1 fM to about 1 μM.

107. The kit according to any of embodiments 61-106, wherein the one or more nucleic acid agents identified as having a desired property binds to the target moiety with a $K_{DT}$ and binds to the reference moiety with a $K_{DR}$, and a ratio between the $K_{DR}$ and the $K_{DT}$ is from about $10^2$ to $10^{12}$.

108. The kit according to any of embodiments 61-107, wherein the one or more nucleic acid agents identified as having a desired property binds to the target moiety with a first apparent $K_{DT}$ when the binding occurs in a composition comprising said target moiety but not said reference moiety, and the one or more nucleic acid agents identified as having the desired property binds to the target moiety with a second apparent $K_{DT}$ when the binding occurs in a composition comprising both said target moiety and said reference moiety, and wherein a difference between said first apparent $K_{DT}$ and said second apparent $K_{DT}$ is less than about 20% of the value of the first apparent $K_{DT}$.

109. The kit according to any of embodiments 105-108, wherein the component for generating an enriched mixture of candidate nucleic acid agents comprises devices and/or agents for conducting nucleic acid amplification.

110. The kit according to embodiment 109, wherein said nucleic acid amplification comprises PCR or reverse transcriptase PCR.

111. The kit according to any of embodiments 61-110, further comprising an agent and/or a device for conducting emulsion PCR to immobilize the mixture of candidate nucleic acid agents onto the plurality of particle.

112. The kit according to any of embodiments 61-111, wherein the target moiety comprises a protein or a part thereof selected from the group consisting of Tumor Necrosis Factor α, Neutrophil Gelatinase-Associated Lipocalin, Histidine-Rich Protein 2, Platelet-Derived Growth Factors, Vascular Endothelial Growth Factors, Angiopoietins, Complement proteins and Integrins.

113. The kit according to any of embodiments 61-112, wherein the reference moiety comprises one or more molecules homologous to the target moiety.

114. The kit according to any of embodiments 113, wherein the one or more molecules have a homology of 50%~99% to the target moiety.

115. The kit according to any of embodiments 61-114, wherein the reference moiety comprises a mixture comprising proteins, glycans and/or small molecules.

116. The kit according to any of embodiments 61-115, wherein the reference moiety comprises a mixture comprising blood, plasma, serum, liquid humor, vitreous, urine, tissue fluid, spit, and/or saliva.

117. The kit according to embodiment 116, wherein the blood, plasma, serum, liquid humor, vitreous, urine, tissue fluid, spit, and/or saliva is from a human being.

118. A pool of particles comprising from about $1 \times 10^2$ to about $1 \times 10^{14}$ particles, each particle from the pool has immobilized thereon from about $1 \times 10^2$ to about $1 \times 10^{10}$ copies of single stranded nucleic acid agents comprising a single nucleic acid sequence;
wherein sequence diversity of the pool of particles is less than the number of particles in the pool;
each particle from the pool has at least one dimension of from about 50 nm to about 100 μm; and
wherein the single stranded nucleic acid agents immobilized on the particles bind to a target moiety with a $K_{DT}$ and binds to a reference moiety with a $K_{DR}$, the $K_{DT}$ is from about 1 fM to about 1 μM and a ratio between the $K_{DR}$ and the $K_{DT}$ is from about $10^2$ to $10^{12}$.

119. The pool of particles according to embodiment 118, wherein the single stranded nucleic acid agents immobilized on the particles bind to the target moiety with a first apparent $K_{DT}$ when the binding occurs in a composition comprising said target moiety but not said reference moiety, and the single stranded nucleic acid agents immobilized on the particles bind to the target moiety with a second apparent $K_{DT}$ when the binding occurs in a composition comprising both said target moiety and said reference moiety, and wherein a difference between said first apparent $K_{DT}$ and said second apparent $K_{DT}$ is less than about 20% of the value of the first apparent $K_{DT}$.

120. The pool of particles according to any of embodiments 118-119, wherein the target moiety is a protein or a polypeptide moiety.

121. The pool of particles according to any of embodiments 118-120, wherein the reference moiety is a protein or a polypeptide moiety.

122. The pool of particles according to embodiment 121, wherein the reference moiety comprises serum proteins.

123. The pool of particles according to any of embodiments 118-122, wherein the single stranded nucleic acid agent is selected from a DNA molecule, a RNA molecule, a chemically modified DNA molecule, and a chemically modified RNA molecule.

124. The pool of particles according to embodiment 123, wherein the single stranded nucleic acid agent is a DNA molecule.

125. The pool of particles according to any of embodiments 118-124, wherein the single stranded nucleic acid agent comprises one or more non-natural nucleic acid.

126. The pool of particles according to any of embodiments 118-125, wherein one or more of the single stranded nucleic acid agents comprises a molecule conjugated thereto.

127. The pool of particles according to embodiment 126, wherein the molecule conjugated to one or more of the single stranded nucleic acids is a small molecule, a fluorophore, a peptide, and/or an siRNA.

128. The pool of particles according to any of embodiments 118-127, wherein said desired property is an ability to specifically bind to a target or an activity induced by such specific binding.

129. The pool of particles according to embodiment 128, wherein the activity induced by such specific binding is a catalytic activity, a modified catalytic activity, an inhibition activity, an activation activity, a modification of an inhibition activity, an activation activity, a structure switching activity, a modification of a structure switching activity, and/or a cooperative activity.

130. The pool of particles according to any of embodiments 118-129, wherein said particle is non-magnetic, magnetic or paramagnetic.

131. The pool of particles according to any of embodiments 118-130, wherein each of said plurality of particles has at least one dimension of from about 50 nm to about 100 μm.

132. The pool of particles according to any of embodiments 118-131, wherein said plurality of particles comprise carboxylic acid paramagnetic particles having an average diameter of about 1 μm.

133. The pool of particles according to any of embodiments 118-132, wherein each of the single stranded nucleic acid agents is coupled to a particle of the pool via a linker.

134. The pool of particles according to embodiment 133, wherein the linker is a cleavable linker, a non-cleavable linker or a combination thereof.

135. The pool of particles according to any of embodiments 133-134, wherein the linker is an amino-modified nucleic acid primer.

136. The pool of particles according to any of embodiments 118-135, wherein the single stranded nucleic acid agent is an aptamer.

137. The pool of particles according to any of embodiments 118-136, wherein the target moiety comprises a protein or a part thereof selected from the group consisting of Tumor Necrosis Factor α, Neutrophil Gelatinase-Associated Lipocalin, Histidine-Rich Protein 2, Platelet-Derived Growth Factors, Vascular Endothelial Growth Factors, Angiopoietins, Complement proteins and Integrins.

138. The pool of particles according to any of embodiments 118-137, wherein the reference moiety comprises one or more molecules homologous to the target moiety.

139. The pool of particles according to any of embodiments 138, wherein the one or more molecules have a homology of 50%~99% to the target moiety.

140. The pool of particles according to any of embodiments 118-139, wherein the reference moiety comprises a mixture comprising proteins, glycans and/or small molecules.

141. The pool of particles according to any of embodiments 118-140, wherein the reference moiety comprises a mixture comprising blood, plasma, serum, liquid humor, vitreous, urine, tissue fluid, spit, and/or saliva.

142. The pool of particles according to embodiment 141, wherein the blood, plasma, serum, liquid humor, vitreous, urine, tissue fluid, spit, and/or saliva is from a human being.

143. The pool of particles according to embodiment 137, wherein the target moiety comprises Tumor Necrosis Factor α or a part thereof, and the single stranded nucleic acid agents immobilized on the particles comprises a sequence as set forth in SEQ ID NO: 1.

144. The pool of particles according to embodiment 137, wherein the target moiety comprises Neutrophil Gelatinase-Associated Lipocalin or a part thereof, and the single stranded nucleic acid agents immobilized on the particles comprises a sequence as set forth in SEQ ID NO: 3.

145. The pool of particles according to embodiment 137, wherein the target moiety comprises Histidine-Rich Protein 2 or a part thereof, and the single stranded nucleic acid agents immobilized on the particles comprises a sequence as set forth in SEQ ID NO: 4.

The sequences employed in the present disclosure are summarized in the table below:

TABLE 1

Sequence Listing

| Sequence ID | Sequence |
|---|---|
| 1 | ATCCAGAGTG ACGCAGCATG CTTAAGGGGG GGGCGGGTTA AGGGAGTGGG GAGGGAGCTGGTGTGGACAC GGTGGCTTAG T |
| 2 | ATCCAGAGTG ACGCAGCAGG TTAAGGTGTA GGTCCGGGTG GGGGGGTGGG TTGGGGGACT GGTGGACACG GTGGCTTAGT |
| 3 | GAATTCCGCC CTCGTCCCAT CTCGGCTTGG TATGGCGGAG CTGGATAGTA TAGTCGGAAC ACCAACCGAG AACGGAATTC |
| 4 | ATCCAGAGTG ACGCAGCATT AAATAGGGGT TTGGCTTTGG GTCTGGCATA TAGGAACAAG TTTGGACACG GTGGCTTAGT |
| 5 | ATCCAGAGTG ACGCAGCA-[44N]-TGGACACG GTGGCTTAGT |
| 6 | GAATTCCGCC CTCGTCCCAT CTC-[34N]-AAC ACCAACCGAG AACGGAATTC |
| 7 | amino-PEG 18-ATCCAGAGTG ACGCAGCA |
| 8 | amino-PEG 18-GAATTCCGCC CTCGTCCCAT CTC |

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s) and the like.

Materials

Single-stranded DNA (ssDNA) library, primers and selected nucleic acid agent sequences were purchased from Integrated DNA Technologies (IDT). The library was synthesized with hand mixing and PAGE-purified. For screening against TNF-α and HRP-2, each 80 nt library member featured a 44 nt randomized sequence flanked by 18 nt PCR primer sites (SEQ ID No. 5: 5'-ATCCAGAGTGACGCAGCA-[44N]-TGGACACGGTGGCTTAGT-3'). For screening against NGAL, each 80-nt library member featured a 34-nt randomized sequence flanked by 23-nt PCR primer sites (SEQ ID NO. 6: 5'-GAATTCCGCCCTCGTCCCATCTC-[34N]-AACACCAACCGAGAACGGAATTC-3'). Unlabeled, 5'-amino-modified and Alexa Fluor 488-modified PCR primers were obtained from IDT with high-performance liquid chromatography (HPLC) purification. Recombinant human TNF-α protein (with and without biotinylation) and recombinant human NGAL protein were purchased from R&D Systems, and the recombinant Malaria HRP-2 protein was purchased from Fitzgerald Industries International. The labeling antibody for TNF-α MPPD screening (AlexaFluor 488-labeled anti-human TNF-α MAb11) was purchased from eBioscience, and the labeling antibody for NGAL and HRP-2 MPPD screening (iFluor 488-labeled anti-His-Tag monoclonal antibody) was purchased from GenScript. The anti-human TNF-α monoclonal antibody pair used in the ELISA assay (MAb11 and MAb1) were also purchased from eBioscience.

Methods for the Preparation Before Performing the Screening According to the Present Disclosure:

A. Pre-Enrichment by SELEX to Obtain Nucleic Acid Agents Suitable to be Immobilized onto the Plurality of Particles:

During the first pre-enrichment SELEX round for TNF-α, $6\times10^{14}$ random DNA molecules were incubated with about 200 nM of biotinylated TNF-α (purchased from R&D Systems) in PBSMCT (DPBS with 2.5 mM $MgCl_2$, 1 mM $CaCl_2$, 0.01% TWEEN-20) in a 100 µl reaction for 3 hours. 50 µl of Dynabeads MyOne Streptavidin C1 (purchased from Life Technologies) 1 µm beads were washed with PBSMCT twice. After incubation, the DNA and TNF-α mixture was added to the streptavidin beads, and incubated for 15 minutes. The beads were washed three times with 500 µl of PBSMCT for 5 minutes. The TNF-α-bound DNA molecules were then eluted by adding 100 µl PCR grade water and heating at 95° C. for 5 minutes. The eluted DNA was PCR amplified and used for synthesizing particles immobilized with candidate nucleic acid sequences.

Similar methods were adopted for the pre-enrichment SELEX rounds for NGAL and HRP-2, and the concentration of target moiety used for pre-enrichment was 500 nM and 100 nM for NGAL and HRP-2, respectively. Because both the recombinant NGAL and HRP-2 have His-Tag attached to them, 50 µl of Dynabeads His-Tag isolation and pulldown (purchased from Life Technologies) 1 µm beads were used, instead of MyOne Streptavidin C1 beads, for capturing the target protein and target bound candidate nucleic acid agents.

B. Coupling Forward Primers (FP) to Particles to Obtain Particles Suitable for Particles Immobilized with Candidate Nucleic Acid Agents:

1 ml of 1 µm MyOne carboxylic acid magnetic particles ($10^7$/µl, purchased from Life Technologies) were washed once with 1 ml of 0.01N NaOH and three times with 1 mL of nuclease-free water, then resuspended in a 300 µl reaction mixture containing 200 mM NaCl, 0.2 mM 5'-amino-modified FP (SEQ ID NO.7: 5'-amino-PEG18-ATCCAGAGTGACGCAGCA-3' or SEQ ID NO.8: 5'-amino-PEG18-GAATTCCGCCCTCGTCCCATCTC-3'), 1 mM imidazole chloride, and 250 mM EDC (Pierce Biotechnology). Amino group modification enables covalent coupling, keeping FPs attached to the particles during thermal cycling, with the PEG18 at the 5' end serving as a spacer. Particles and reagents were mixed well, vortexed, sonicated and incubated overnight at room temperature (RT) on a rotator. To reduce non-specific interaction with target molecules, free carboxyls on the particles into amino-reactive NHS-ester in the presence of 250 mM EDC and 100 mM N-hydroxysuccinimide (NHS) were converted to 2-(N-morpholino) ethanesulfonic acid (MES) buffer (100 mM, PH 4.7) (Pierce Biotechnology) for 30 minutes at RT. The particles were then conjugated with 20 mM amino-PEG12 (Pierce Biotechnology) in MES buffer for one hour. The particles were washed twice for 30 minutes with 1 ml of TT buffer (250 mM Tris, 0.1% Tween 20, pH 8.0), suspended in 1 ml of TE buffer (10 mM Tris, pH 8.0, 0.1 mM EDTA), and stored at 4° C.

C. Synthesis of Particles Immobilized with Candidate Nucleic Acid Agents:

Emulsion PCR: The oil phase (prepared fresh every week) was composed of 4.5% Span 80, 0.40% Tween 80 and 0.05% Triton X-100 in mineral oil, all purchased from Sigma-Aldrich. The aqueous phase consisted of 1× GoTaq PCR Master Mix (purchased from Promega), 25 mM $MgCl_2$, 3.5 mM of each dNTP (purchased from Promega), 3 µM reverse primer (purchased from PRP), 0.5 U/µl of GoTaq Hot Start Polymerase (purchased from Promega), 2 pM template DNA, and $3\times10^8$ FP-coated particles in a total volume of 1 ml. Water-in-oil emulsions were prepared by adding 1 ml of the aqueous phase to 7 ml of oil phase in a DT-20 tube (purchased from IKA) locked into the Ultra-Turrax Device (purchased from IKA). This addition was performed drop-wise over 30 seconds while the mixture was being stirred at 650 rpm in the Ultra-Turrax. After adding the aqueous phase, the mixture was stirred continually for 5 min. The emulsions were distributed in 100 µl aliquots into about 80 wells of a 96-well PCR plate. PCR was performed under the following cycling conditions: 95° C. for 3 min, followed by 50 cycles of 95° C. for 15 sec, 60° C. for 30 sec and 72° C. for 75 sec.

Emulsion PCR cleanup: After PCR, 50 µl of 2-butanol was added into each PCR well and mixed well to break the emulsion. The broken emulsions were then transferred to a 50 ml tube. Next, 150 µl of 2-butanol was added to each PCR well to collect the leftover emulsions and transferred to the 50 ml collection tube. After vortexing for 30 sec, the particles were pelleted by centrifugation at 2,500×g for 5 min. After carefully removing the oil phase, the particles were resuspended in 1 ml of emulsion breaking (EB) buffer (100 mM NaCl, 1% Triton X-100, 10 mM Tris-HCl, pH 7.5, and 1 mM EDTA) and transferred to a new 1.5 ml tube. After vortexing for 30 sec and centrifugation for 90 sec at 15,000× g, and the supernatant was removed. The tube was then placed on a magnetic separator (MPC-S, purchased from Life Technologies), and remaining supernatant was pipetted off. Particles were washed three times with TE buffer using magnetic separation, then were resuspended in 300 µl TE.

Single strand generation: To generate single-stranded DNA, the particles were magnetically concentrated for 1 min, and removed the supernatant with a pipette tip. Then the particles were resuspended in 200 µl of 100 mM NaOH and incubated at 50° C. for 2 min. The tube was placed in the magnetic separator for 1 min and the supernatant was carefully removed. After repeating this step twice, the particles were resuspended in 300 µl TE.

D. Quality Control for Candidate Nucleic Acid Agent Immobilized Particle:

Forward primer conjugation: To test conjugation efficiency of the forward primers, 1 µM Alexa Fluor 488-modified FP complementary sequence (purchased from FPC) was incubated with 0.2 µl of FP particles in 100 µl of STE buffer (10 mM Tris pH 8.0, 50 mM NaCl, 1 mM EDTA) at 55° C. for 10 minutes, then snap was cooled on ice for 2 minutes. The particles were washed twice with 100 µl TE buffer and analyzed with a Accuri C6 Flow Cytometer (purchased from BD Biosciences).

Candidate nucleic acid agent immobilized particle monoclonality: Based on the Poisson distribution, it is predicted that most particles would be monoclonal when <35% of the particles contain PCR products. To confirm this, the candidate nucleic acid agent immobilized particles were annealed with AlexaFluor 488-labeled RP in STE buffer at 55° C. for 10 minutes and snap-cooled on ice for 2 minutes. The particles were then washed twice with 100 µl TE buffer and analyzed by flow cytometry.

Determining candidate nucleic acid agent copy number on each candidate nucleic acid agent particle: Quantitative PCR (qPCR) was performed with an CFX96 Touch Real-Time PCR Detection System (purchased from Bio-Rad) to estimate candidate nucleic acid agent copy number for each AP (Candidate nucleic acid agent particle). Calibration samples were prepared by adding $10^6$, $10^7$, $10^8$, $10^9$ or $10^{10}$ templates into a 20 µl reaction containing 250 nM each of FP and RP, 1,000 FP-coated particles, 10 µl GoTaq PCR Master Mix (purchased from Promega) and 0.5× SYBR green (purchased from Life Technologies). Test samples were prepared identically, but with 1,000 Aps. From the threshold cycle, it was quantified that $4.8\times10^7$ sequences on 1,000 APs. Since only about 20% of APs displayed template sequences, the average copy number of sequences on each template-bearing AP was about $2\times10^5$.

E. Biotinylation of Human Serum for Performing the Screening:

Human serum was purchased from Fitzgerald Industries International. Serum proteins were biotinylated using the EZ-Link Micro NHS-PEO$_4$-Biotinylation Kit (purchased from Pierce Biotechnology), which includes a polyethylene glycol (PEG) spacer to improve water-solubility. Serum was diluted twice with PBS such that the protein concentrations were adjusted to about 40 mg/ml prior to biotinylation. The average molecular weight of serum protein is estimated to be 150 kDa, and a 45-fold molar excess of NHS-PEO$_4$-Biotin was used to label the serum protein for 30 minutes at room temperature. The free biotin was removed via Zeba Desalt Spin Column with 7K molecular weight cut off (10 ml, purchased from Pierce Biotechnology). Biotinylated serum protein concentration was measured based on absorbance at 280 nm using a NanoDrop spectrophotometer (purchased from Thermo Scientific).

Methods for the Verification after Screening According to the Method of the Present Disclosure:

A. Cloning and Sequencing:

After four rounds of screening against TNF-α, the fluorescence intensities of the candidate nucleic acid agents in the selected pool changed as a uniform population when the concentration of the target was adjusted, indicating convergence of the selected candidate nucleic acid agent sequences. E. coli cloning and sequencing was performed to obtain individual candidate nucleic acid agents from the Round 4 pools from both buffer- and serum-screens and picked 20 clones from each pool. Since >90% of candidate nucleic acid agents in each selected pool essentially converged to one unique candidate nucleic acid agent sequence, only the dominant candidate nucleic acid agent sequence was picked for K$_D$ (equilibrium dissociation constant) measurement and further analysis.

Same approach was applied for subsequent screenings for NGAL (5 rounds) and HRP-2 (7 rounds). The dominant candidate nucleic acid agent sequences for each screening were as set forth in SEQ ID NO.1 (S01, TNF-α in serum), SEQ ID NO.2 (B01, TNF-α in buffer), SEQ ID NO.3 (NGAL-05, NGAL in serum), or SEQ ID NO.4 (HRP-2-702, HRP-2 in serum), respectively.

B. Affinity Measurement:

MyOne carboxylic acid magnetic particles were coated with amino-modified candidate nucleic acid agents S01, B01, or VR11 (a previously published TNF-α candidate nucleic acid agent), or with mAb11 antibody (a commercial TNF-α antibody). For affinity measurement, different concentrations of biotinylated TNF-α (25 pM to 25.6 nM) were incubated with a fixed amount of the candidate nucleic acid agent- or antibody-coated particles ($10^4$ particles/ml) in 300 µl PBSMCT for 3 hours at room temperature. The unbound TNF-α was washed away with PBSMCT, after which streptavidin-conjugated Alexa Fluor 488 was introduced and incubated for 15 minutes to label the bound TNF-α. The particles were washed with PBSMCT and median fluorescence intensities were quantified via FACS.

The similar method was applied for measuring the affinity of the NGAL-05 and HRP-2702 candidate nucleic acid agents. Instead of the streptavidin-conjugated Alexa Fluor 488, iFluor 488 His-Tag antibody was introduced and incubated for 30 minutes to label the bound NGAL or HRP-2.

C. ELISA

Homogeneous ELISA was performed using mAb11 as the capture antibody, with biotinylated S01 or matching antibody mAb1 as the detection reagent. 50 µl of mAb11 (5 µg/ml in PBS) was added to each well of a 96-well plate, which was then sealed with parafilm and incubated overnight at 4° C. to coat the wells. The plate was blocked with AptaBuffer (PBSMCT+0.1 mg/ml salmon sperm DNA+0.5 mg/ml dextran sulfate) for 30 minutes at room temperature. Then TNF-α was added at multiple concentrations (0, 0.025, 0.05, 0.1, 0.2, 0.4, 0.8, 1.6, 3.2 ng/ml) and then detection reagent—either 40 nM biotin-S01 or 1 µg/µl of biotin-MAb1 was pre-incubated with 10 nM streptavidin-conjugated horseradish peroxidase (HRP), and was incubated at room temperature for 1 hour. Four washes with PBST (PBS+0.1% Tween 20) were performed to remove unbound TNF-α and detection reagents, and then 50 µl of tetramethylbenzidine (TMB) was added to each well for detection. Finally, the absorbance of each well at 450 nm was measured to determine the signal.

Example 1

Theoretical Analysis

In order to isolate candidate nucleic acid agents (e.g., aptamers) that simultaneously exhibit high affinity and specificity, it is critical to impose an appropriate 'sorting range' so that these candidate nucleic acid agents can be selected from the vast background of the candidate nucleic acid agent library. Two important experimental parameters that govern the sorting range are the concentration of the target moiety [T] and the reference moiety [R]. This is because these two parameters may dramatically shift the binding of the candidate nucleic acid agent population either toward the target or the reference moiety. To provide a detailed theoretical analysis of this dependence, the binding interaction between a candidate nucleic acid agent (C) and its target (T) in a complex environment of reference moiety [R] can be effectively described in terms of the binding fraction (BF). The BF is defined in Eq. 1.

$$BF = \frac{[T]}{[T] + K_{DT} \cdot \left(1 + \frac{[R]}{K_{DR}}\right)}. \qquad \text{Eq. 1}$$

$K_{DT}$ and $K_{DR}$ are the equilibrium dissociation constants of the candidate nucleic acid agent for the target moiety and the reference moiety, respectively, and are inherent properties of a candidate nucleic acid agent. As $K_{DR}/K_{DT} \rightarrow 0$ (candidate nucleic acid agent binds non-specifically to reference moieties), BF approaches 0, and as $K_{DR}/K_{DT} \rightarrow \infty$ (candidate nucleic acid agent only binds to the target), the BF approaches the Langmuir isotherm.

On the other hand, [T] and [R] are external parameters that directly affect the BF. Because these two parameters are independent of each other, there are innumerable combinations that shift the binding of a candidate nucleic acid agent toward the target moiety or the reference moiety. Furthermore, given that the $K_{DT}$ and $K_{DR}$ of candidate nucleic acid agents in a large population are not known in the prior art, it is not possible to predict the combination of [T] and [R] that will yield populations of candidate nucleic acid agents with high BF.

To provide an example, this dependence of different candidate nucleic acid agent's binding behavior on its inherent properties and the environment is illustrated in FIGS. 2A-2D, which depicts a theoretical pool of candidate nucleic acid agents being measured according to its target and non-target binding (x- and y-axes). Each candidate nucleic acid agent has a unique combination of $K_{DT}$ and $K_{DR}$, as depicted by the different shapes in the grid legend of FIGS. 2A-2D. Then four combinations of [R] and [T] were examined to reveal how the population shifts in response. By varying these conditions, it is determined that only a limited set of conditions yields candidate nucleic acid agents with the desired affinity and specificity. All other conditions either make it impossible to eliminate low affinity or specificity candidate nucleic acid agents or over-discriminate and eliminate good binders as well as poor binders.

Figure 2:
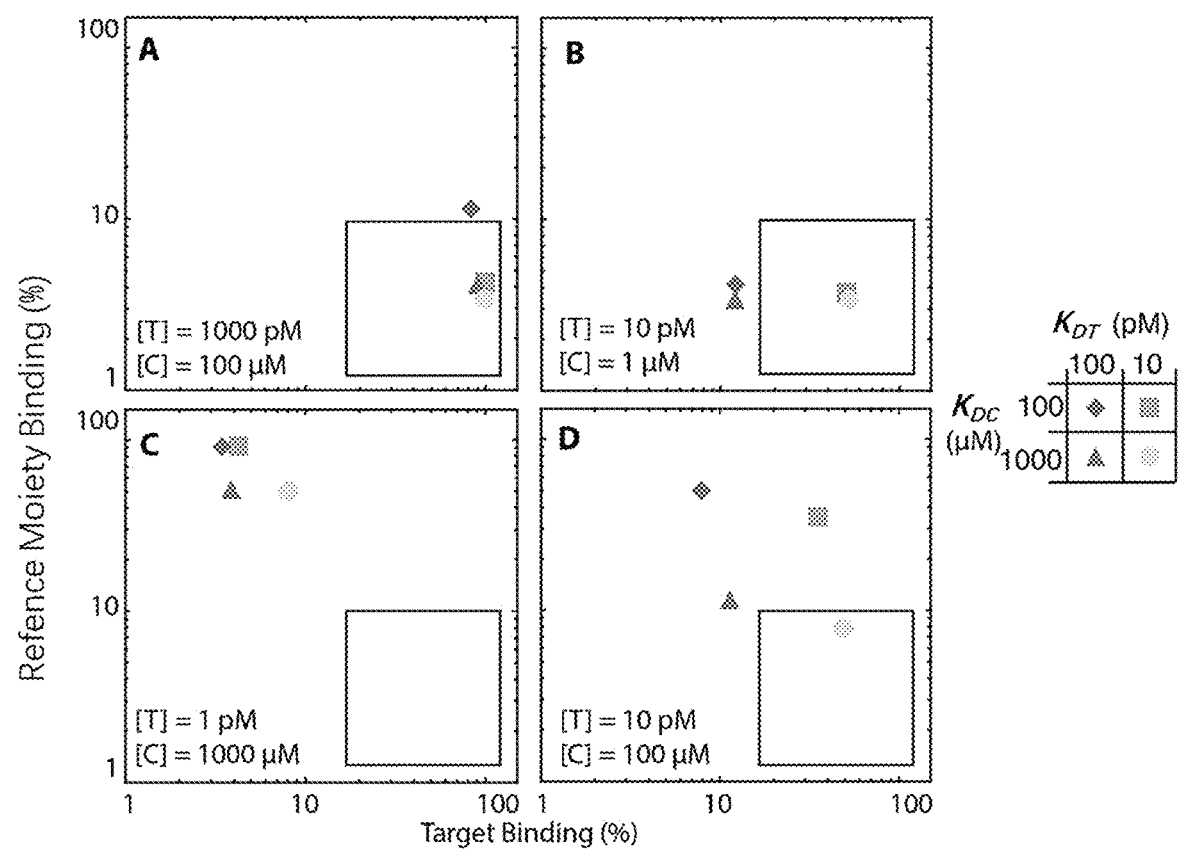
FIGS. 2A-2D illustrates a modeling process for performing a method of the present application with different concentrations of target moiety and reference moiety.

A critical deficiency of conventional SELEX is its inability to identify combinations of [T] and [R] that will reproducibly yield candidate nucleic acid agents that simultaneously exhibit high affinity and specificity. The method of the present disclosure offered the unprecedented means to directly visualize the binding behavior of every candidate nucleic acid agent in a given library as varying [T] and [R], so that the optimal stringency (i.e., sorting range) can be applied (FIG. 2D). In FIGS. 2A-2D, plots depict a theoretical pool containing four candidate nucleic acid agents with varying affinity to the target moiety ($K_{DT}$) or non-target reference moiety ($K_{DR}$). The x-axis represents target binding and the y-axis represents reference moiety binding, both of which are determined by [R] and [T] as well as $K_{DT}$ and $K_{DR}$. Ideally, only the desired high-affinity and specificity candidate nucleic acid agents (represented by a round dot) should reside within the "sorting range" in the lower right quadrant of each plot (represented as a black box) and this can be accomplished by varying [T] and [R] to influence the binding of the candidate nucleic acid agent population. This made it possible for the method of the present disclosure to reproducibly generate highly specific candidate nucleic acid agents also with high affinity.

Figure 3:
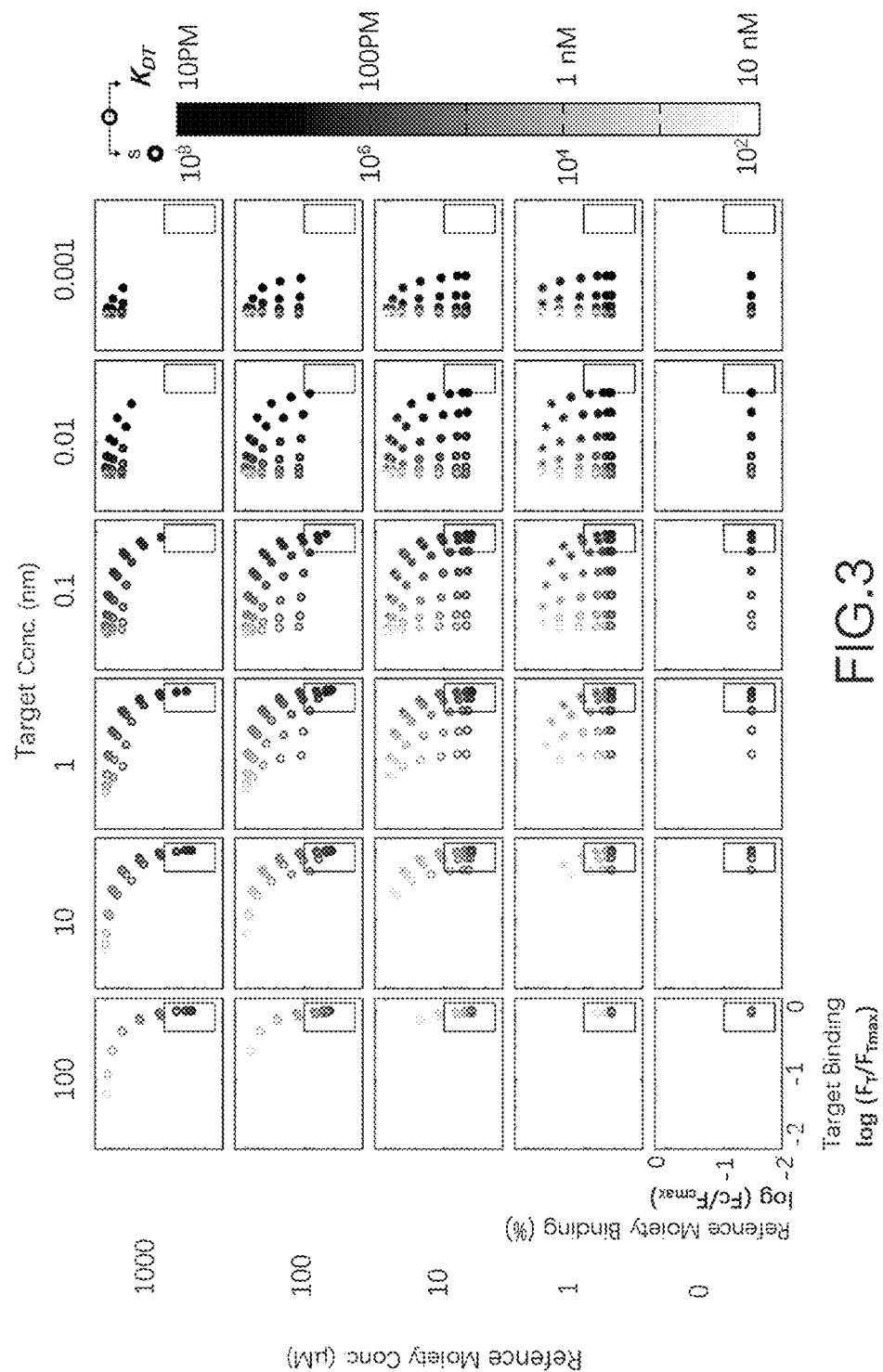
FIG. 3 illustrates the identification result of a method according to the present application with different combinations of target concentration and reference moiety concentration.

Next, a screening of a candidate nucleic acid agent pool under various different combinations of [R] and [T] was simulated. In FIG. 3, the simulation results of a pool of candidate nucleic acid agents exhibiting its target and non-target binding (x- and y-axes) under different environments, and a sorting range (black box) are illustrated. Each candidate nucleic acid agent has a unique combination of $K_{DT}$ and $K_{DR}$. The specificity (S) of a candidate nucleic acid agent was represented as the ratio of $K_{DR}/K_{DT}$, and each candidate nucleic acid agent was represented by its $K_{DT}$ and its S value. The $K_{DT}$ and S were bounded by 10 nM-10 pM, and $10^2$-$10^8$, respectively. Thirty different combinations of [R] and [T] were applied to the pool, which revealed how the population shifts in response. These plots showed that it is critical to optimize multiple conditions to discriminate and isolate the ideal subpopulation of binders.

Based on the above theoretical analysis, a set of simple principles for determining the optimal screening condition were arrived at. The sorting range was set so that the target binding fluorescence was above about one half of the maximum mean fluorescence when a candidate nucleic acid agent immobilized particle was saturated with fluorescent targets moiety, and the reference moiety binding fluorescence was below about one tenth of the maximum mean fluorescence when a candidate nucleic acid agent immobilized particle was saturated with labeled reference moiety (i.e., serum, homologous protein), as shown in FIG. 3.

In FIG. 3, in each plot, the x- and y-axes corresponds to the fraction of candidate nucleic acid agent bound to the target, and reference moieties respectively. Individual candidate nucleic acid agents are represented by donuts. The donut ring and center correspond to the specificity (S) and affinity ($K_{DT}$) of the candidate nucleic acid agent respectively. Stringency for affinity is increased from left to right, and stringency for specificity is increased from bottom to top. Changing target moiety concentration shifts the candidate nucleic acid agents to different positions on the FACS plot, condensing them or separating them from others in the pool. For example, in the absence of the reference moiety, all candidate nucleic acid agents collapse onto a single line, and it is impossible to differentiate specific binders from non-specific binders. As the reference moiety concentration is increased and target moiety concentration is decreased, candidate nucleic acid agents that possess high affinity and specificity begin to emerge distinctly in the lower right corner of the population. If the affinity and specificity stringency are too high, there is risk of losing the highest performance candidate nucleic acid agents (top row, and right column).

Then monitored the fluorescence distribution of the particles at a range of different combination of [T] and [R] and chose the condition at which about 0.1% of the particles resided in the sorting range. By performing screening under the above condition, candidate nucleic acid agents with e.g., $K_{DT}<[T]$ and $S>5\times[R]/[T]$ may be isolated after FACS sorting.

Example 2

Screening for TNFα Specific Binders

A. Screening for TNFα Specific Binders:

The method according to the present disclosure is depicted generally in FIG. 1A and FIG. 1B. The method comprises: transforming solution-phase candidate nucleic acid agents into candidate nucleic acid agent immobilized particles by covalently conjugating forward PCR primers to magnetic particles (1) and performing emulsion PCR under conditions (2) that produce monoclonal candidate nucleic acid immobilized particles displaying multiple copies of a single sequence (3). These particles are incubated with target moiety and reference moiety labeled with distinct fluorophores (green and red, respectively) (4); then sorted using FACS (5) to isolate particles immobilized with candidate nucleic acids that exhibit high affinity and specificity. These selected nucleic acids are then PCR amplified for additional screening (6) or sequenced for further characterization (7).

More specifically, during each round of screening, about $10^8$ candidate nucleic acid agent immobilized particles were incubated in 1 ml of PBSMCT with target proteins at different concentrations (1-100 nM for TNF-α as the target moiety). Various concentrations of biotinylated human serum were also introduced as the reference moiety to eliminate non-specific binding candidate nucleic acid agents. Since there are proteins in serum that exhibit weak affinity towards negatively charged nucleic acids, 0.1 mg/ml salmon sperm DNA (purchased from Life Technologies) was added to block such nonspecific interactions during each screening rounds. After 1 hour of incubation with the target protein in serum, the beads were washed twice with PBSMCT. Then the candidate nucleic acid agent immobilized particle-captured target proteins were simultaneously labeled with a fluorescently labeled monoclonal antibody (1 nM of Alexa 488 anti-TNF-α MAb11 for TNF-α) and the biotinylated serum with 50 nM streptavidin-conjugated Alexa 647 (Life Technologies) for 20 minutes. The beads were then washed with PBSMCT twice and measured by FACS for the independent Alexa 488 and Alexa 647 signals.

For each round, the effects of different serum concentrations (0%, 0.1%, 0.33%, 1%, 3.3%, and 10%) were tested on candidate nucleic acid agent binding to target proteins. The goal was to identify a serum concentration where the target binding signal remains high enough for effective isolation of high-affinity candidate nucleic acid agents, and where the serum-binding profile of those high-affinity candidate nucleic acid agents shows a wide distribution that makes it easy to separate the candidate nucleic acid agents with the lowest serum affinity.

The 0% serum sample serves as a positive control to demonstrate the target binding signal when no interfering proteins are present. It is also ensured that there was no binding to the antibody label with a zero-target control, which only contained the target moiety-labeling antibody. After collecting the highest-fluorescence candidate nucleic acid agent immobilized particles by FACS, the isolated candidate nucleic acid agents were PCR-amplified to generate an enriched pool for a subsequent round of candidate nucleic acid agent immobilized particle synthesis.

Figure 4:
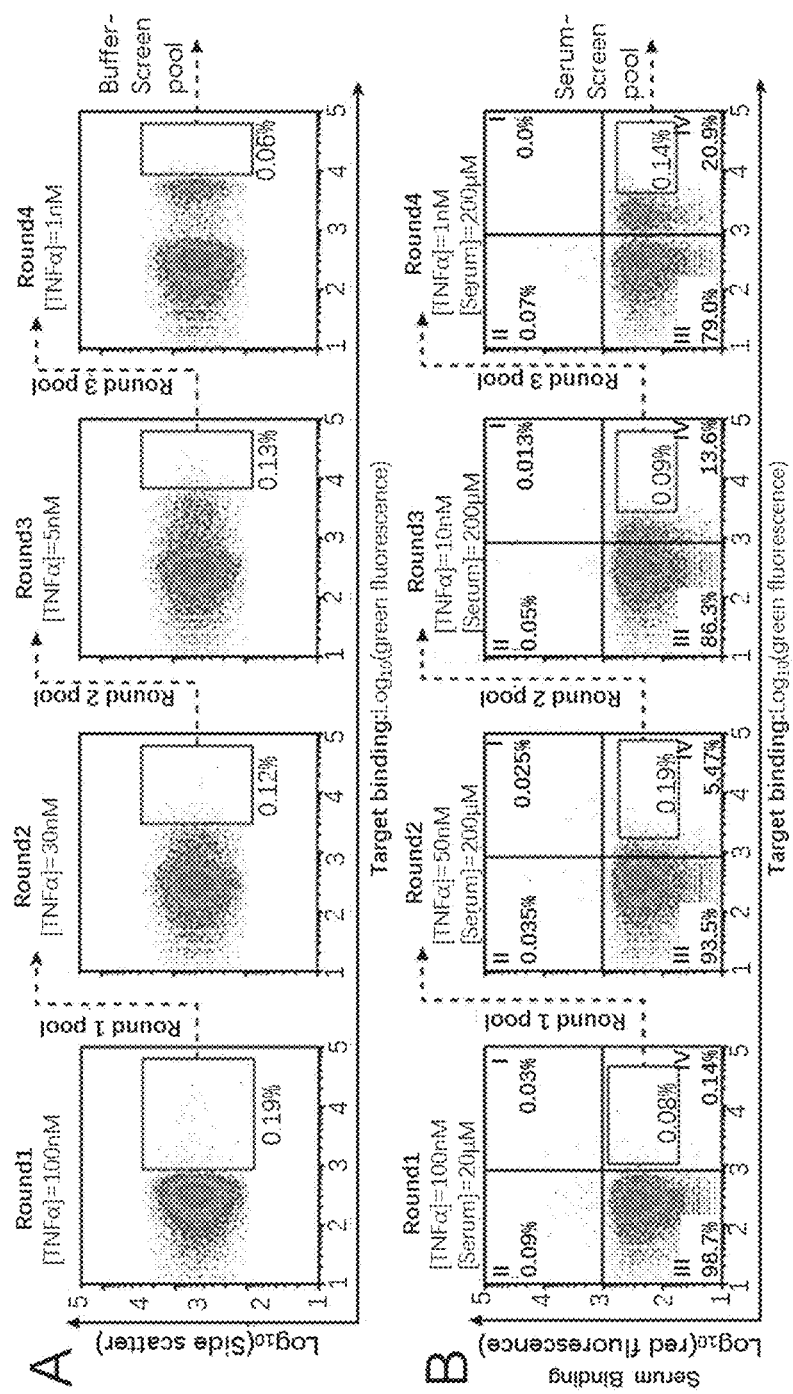
FIGS. 4A-4B illustrate the process of a method according to the present application when TNFα was the target moiety and human serum was used as the reference moiety.

Take the FIGS. 4A-4B for the details. The method according to the present disclosure can be regarded as the process of "serum screen" while the process of "buffer screen" can be regarded as the positive control, and the specificity of the resulting candidate nucleic acid agents were compared. For the 'buffer-screen', four screening rounds in buffer with no reference moieties were performed, starting with 100 nM TNF-α in Round 1 (FIG. 4A). Then 0.19% of the population that exhibited the highest fluorescence was isolated, and then increased the stringency in subsequent rounds by decreasing [T] (30 nM, 5 nM for the second and third round respectively). Candidate nucleic acid agent immobilized particles from Round 4 showed a high fluorescence signal even at 1 nM TNF-α, and 0.06% of the sorted candidate nucleic acid agent immobilized particles in the fourth round was isolated to obtain the final buffer-screen pool. The sorted candidate nucleic acid agent immobilized particle was sequenced and named B01 (SEQ ID NO.2).

For the "serum-screen", four rounds of screening according to the method of the present disclosure were performed in diluted human serum. For Round 1, 100 nM TNF-α and 1% serum (20 μM) were used and sorted 0.08% of the candidate nucleic acid agent immobilized particle population that exhibited high green and low red fluorescence, and in all plots, black boxes show the fraction of candidate nucleic acid agent immobilized particles collected for each round (FIG. 4B). For subsequent rounds, the TNF-α concentration [T] was systematically decreased while the serum concentration [R] was increased. The TNF-α was 50 nM, 10 nM and 1 nM and serum was 200 μM, 200 μM and 200 μM in the round 2, 3 and 4 respectively. In each round, the candidate nucleic acid agent immobilized particle population that exhibited high green and low red fluorescence were sorted. By Round 4, the candidate nucleic acid agent immobilized particles exhibited strong green fluorescence signal even with 1 nM TNF-α in 10% serum.

This is remarkable since the total reference moiety protein concentration in 10% serum (about 0.2 mM) exceeds that of TNF-α by roughly five orders of magnitude. 0.14% of the candidate nucleic acid agent immobilized particles was isolated from Round 4 to obtain the final serum-screen pool. The sorted candidate nucleic acid agent immobilized particle was sequenced and named S01 (SEQ ID NO.1).

Figure 6:
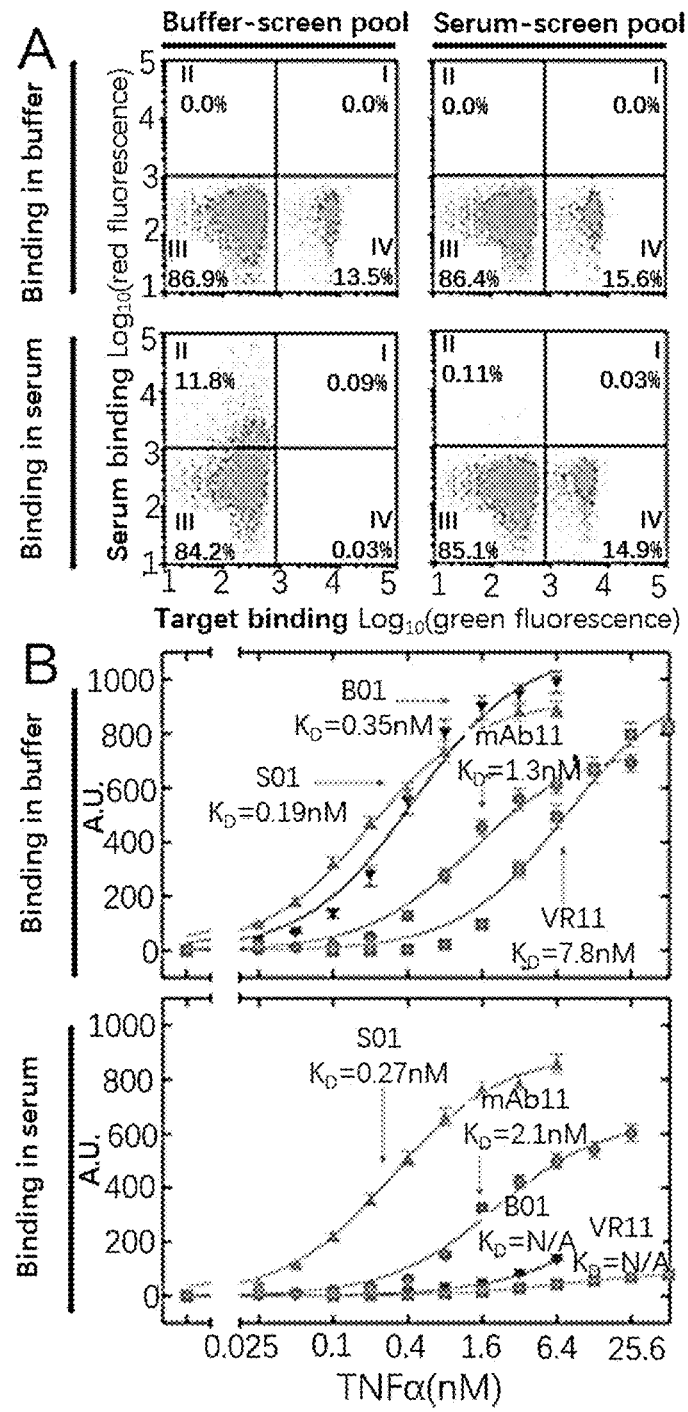
FIGS. 6A-6E illustrate the binding results of various nucleic acid agents identified with a method of the present application.
Figure 6:
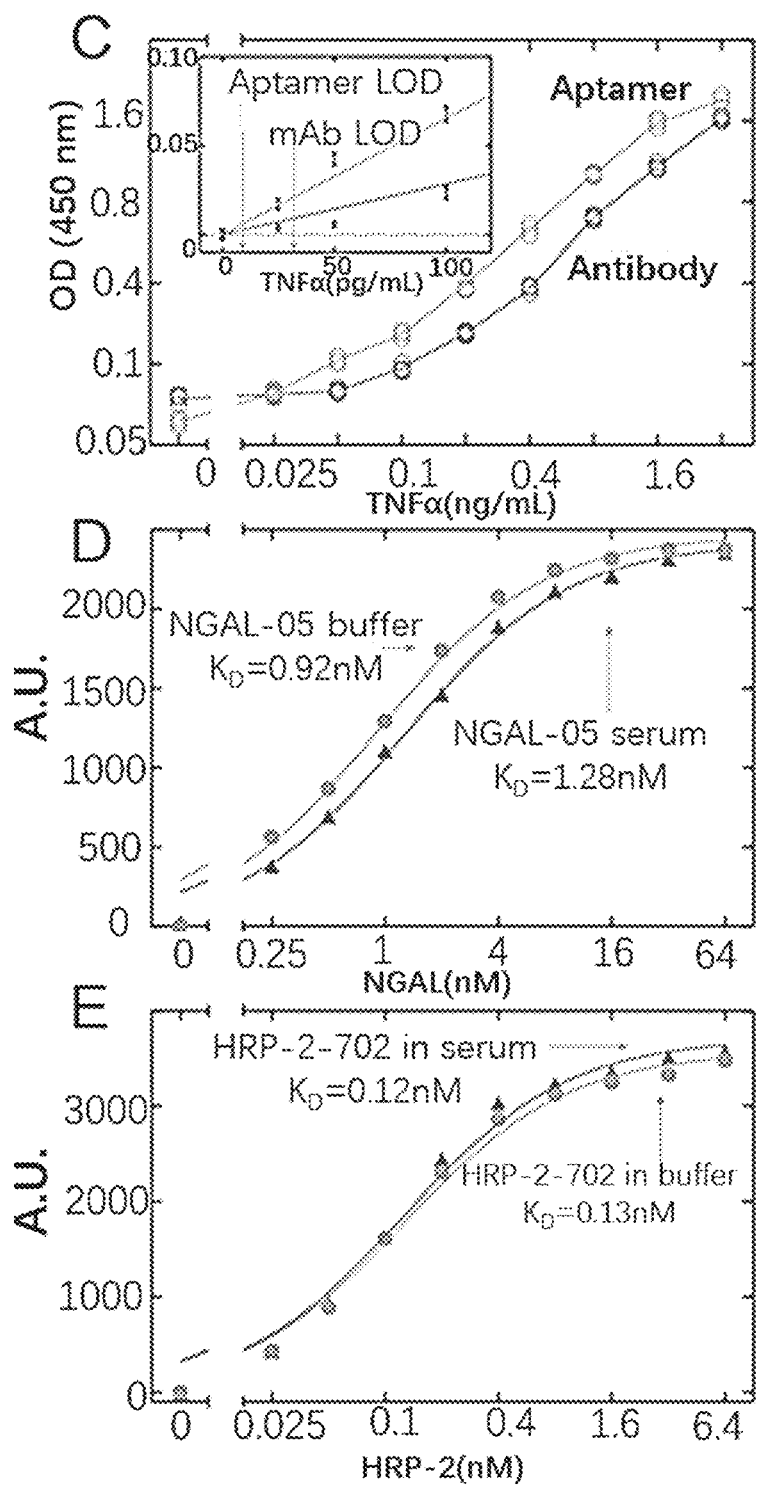

B. Verification of Affinity and Specificity:

The verification results of the present method of selected candidate nucleic acid agents for TNF-α is illustrated in FIGS. 6A-6C. FIG. 6A shows the specificity of candidate nucleic acid agents derived from buffer-screen (left column) and serum-screen (right column), incubated with 1 nM labeled TNF-α either in buffer (top) or 10% human serum (bottom). FIG. 6B shows the binding curves and calculated effective affinities to TNF-α for the top-performing serum-screen (S01) and buffer-screen (B01) candidate nucleic acid agents as well as a known TNF-α aptamer (VR11), and a commercial TNF-α antibody (mAb11). FIG. 6C shows that S01 achieves a superior limit of detection to mAb11 in ELISA assays performed in serum.

In more details, although both pools showed comparable affinity for TNF-α in buffer (FIG. 6A, top), the buffer-screen candidate nucleic acid agents showed poor specificity in serum (FIG. 6A, bottom left). For example, when the buffer-screen candidate nucleic acid agents were challenged with 1 nM TNF-α in 10% human serum, only 0.03% of the candidate nucleic acid agent immobilized particles exhibited modest target binding and low serum binding (quadrant IV). In contrast, the serum-screen pool showed high specificity under identical conditions (FIG. 6A, bottom right), with only a small reduction in the sorted candidate nucleic acid agent population in serum (14.9%) versus buffer (15.6%). In this way, it is shown that the present method can generate candidate nucleic acid agents that specifically bind to TNF-α even among a vast excess of diverse reference moiety proteins.

Individual candidate nucleic acid agent sequences from both pools were cloned, and a fluorescence-based binding assay was used to compare the equilibrium binding constant ($K_D$) of 20 clones from each pool. Sequences and relative affinities of all candidate nucleic acid agents are shown in the methods above. In buffer, the highest-affinity candidate nucleic acid agent from the serum-screen (S01) showed slightly higher affinity ($K_D$=0.19 nM) than its counterpart from the buffer-screen (B01; $K_D$=0.35 nM) (FIG. 6B). Remarkably, the affinity of S01 was essentially unchanged in serum ($K_D$=0.27 nM) compared to that in buffer, clearly demonstrating its exquisite specificity. In contrast, B01 binding virtually disappeared in 10% serum, and hence a meaningful $K_D$ measurement cannot be obtained. Compared S01 with VR11, a known TNF-α candidate nucleic acid agent reported to possess good specificity, in that it does not bind TNF-β, a protein with about 30% sequence homology to TNF-α. VR11 exhibited an affinity for TNF-α of 7.8 nM in buffer, consistent with the reported value (7 nM), but showed minimal target affinity in serum (FIG. 6B), suggesting that even a candidate nucleic acid agent that can differentiate homologous targets may have insufficient specificity to recognize its target in a heterogeneous sample. S01 also exhibited superior performance to a monoclonal antibody currently used in high-sensitivity commercial TNF-α detection assays. mAb11 exhibited the highest affinity and specificity of the various different examined commercial kits, with a $K_D$ of 1.3 nM in buffer and 2.1 nM in 10% serum (FIG. 6D), which is nearly an order of magnitude worse than that of S01 in the same conditions.

S01 was also tested as a potential tool for clinical molecular diagnostics in an enzyme-linked immunosorbent assay (ELISA). The commercial ELISA kit that yielded the best limit of detection (LOD) in 10% serum was selected, with LOD defined as the point on a linear fit of signal to concentration that reaches three times the standard deviation of the signal from a negative control. For comparison, mAb11 was used as the capture reagent and S01 as the detection reagent; these two reagents bind to different epitopes on TNF-α, as mAb 11 was used to label TNF-α during the screening according the method of the present disclosure. The commercial assay yielded a LOD of about 32 pg/ml, consistent with previously reported values, whereas S01-based ELISA exhibited a LOD of about 9.2 pg/ml, an improvement of more than three-fold (FIG. 6C). This is particularly striking given that each detection antibody gains a boost in signal by having multiple (typically >5) biotin labels, allowing it to bind multiple streptavidin HRP reporters, whereas S01 is labeled with just a single biotin.

Example 3

Screening for NGAL Specific Binders

A. Screening for NGAL Specific Binders:

The screening for NGAL using the method of the present disclosure is virtually the same of that for TNF-α, except the followings:

During each round of screening, about $10^8$ candidate nucleic acid agent immobilized particles were incubated in 1 ml of PBSMCT with target proteins at different concentrations (0.5-100 nM for NGAL as the target moiety). Various concentrations of biotinylated human serum were also introduced as the reference moiety to eliminate non-specific binding candidate nucleic acid agents. For NGAL screening, 10 µM of His-Tag peptide (GenScript) was also added to avoid generating candidate nucleic acid agent against the His-Tag attached to the target proteins. After 1 hour of incubation with the target protein in serum, the beads were washed twice with PBSMCT. Then the candidate nucleic acid agent immobilized particle-captured target proteins were simultaneously labeled with a fluorescently labeled monoclonal antibody (5 nM of iFluor 488 His-Tag antibody for NGAL) and the biotinylated serum with 50 nM streptavidin-conjugated Alexa 647 (Life Technologies) for 20 minutes. The beads were then washed with PBSMCT twice and measured by FACS for the independent Alexa 488 and Alexa 647 signals.

Figure 5:
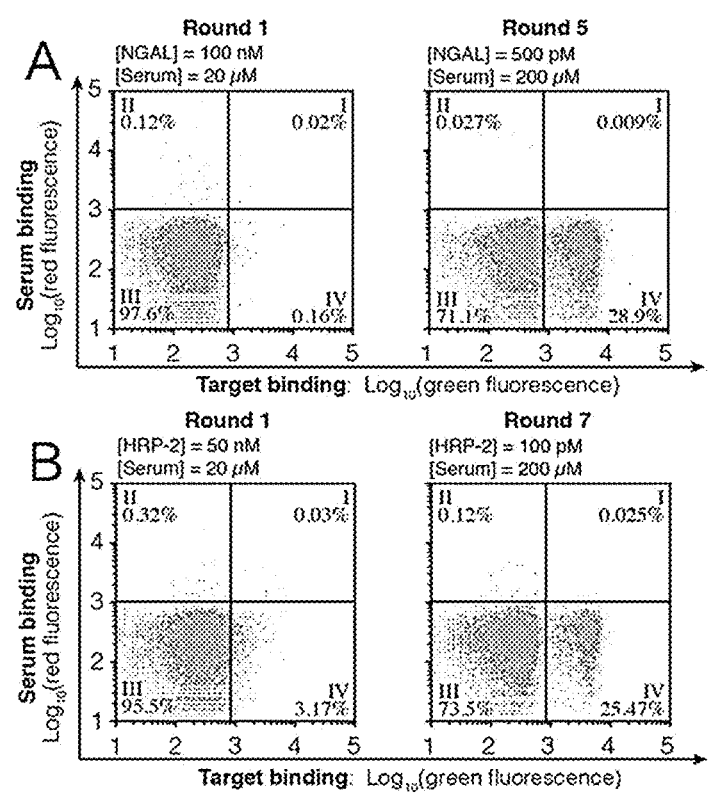
FIGS. 5A-5B illustrate the process of a method according to the present application when NGAL (A) and HRP-2 (B) were respectively used as the target moiety, and human serum was used as the reference moiety.

For the "serum-screen", five rounds of screening according to the method of the present disclosure were performed in diluted human serum. For Round 1, 100 nM NGAL and 1% serum (20 µM) were used and sorted the candidate nucleic acid agent immobilized particle population that exhibited high green and low red fluorescence (FIG. 5A). For subsequent rounds, the NGAL concentration [T] was systematically decreased while the serum concentration [R] was increased. In each round, the candidate nucleic acid agent immobilized particle population that exhibited high green and low red fluorescence were sorted. By Round 5, [T] was 500 pM and [R] was 200 µM. After five rounds of MPPD with decreasing target concentration and increasing reference moiety concentration, 28.9% of the candidate nucleic acid agent immobilized particles showed strong binding in the presence of 500 pM NGAL in 10% serum (FIG. 5A, right).

B. Verification:

The verification results of the method according to the present disclosure of selected candidate nucleic acid agents for NGAL is illustrated in FIG. 6D: an NGAL candidate nucleic acid agent with a $K_D$ of 0.92 nM in buffer and 1.28 nM in serum. In another word, the most abundant candidate nucleic acid agent (NGAL-05) from this pool exhibited a $K_D$ of 920 pM in buffer and 1.28 nM in 10% serum.

Example 4

Screening for HRP-2 Specific Binders

A. Screening for HRP-2 Specific Binders:

The screening for HRP-2 specific binders according to the method of the present disclosure is virtually the same of that for TNF-α, except the followings:

During each round of screening, about $10^8$ candidate nucleic acid agent immobilized particles were incubated in 1 ml of PBSMCT with target proteins at different concentrations (0.1-50 nM for HRP-2 as the target moiety). Various concentrations of biotinylated human serum were also introduced as the reference moiety to eliminate non-specific binding candidate nucleic acid agents. For HRP-2 screening, 10 µM of His-Tag peptide (GenScript) was also added to avoid generating candidate nucleic acid agent against the His-Tag attached to the target proteins. After 1 hour of incubation with the target protein in serum, the beads were washed twice with PBSMCT. Then the candidate nucleic acid agent immobilized particle-captured target proteins were simultaneously labeled with a fluorescently labeled monoclonal antibody (5 nM of iFluor 488 His-Tag antibody for HRP-2) and the biotinylated serum with 50 nM streptavidin-conjugated Alexa 647 (Life Technologies) for 20 minutes. The beads were then washed with PBSMCT twice and measured by FACS for the independent Alexa 488 and Alexa 647 signals.

For the "serum-screen", five rounds of MPPD were performed in diluted human serum. For Round 1, 50 nM HRP-2 and 1% serum (20 µM) were used and sorted the candidate nucleic acid agent immobilized particle population that exhibited high green and low red fluorescence (FIG. 5B). For subsequent rounds, the HRP-2 concentration [T] was systematically decreased while the serum concentration [R] was increased. In each round, the candidate nucleic acid agent immobilized particle population that exhibited high green and low red fluorescence was sorted. By Round 7, [T] was 100 pM and [R] was 200 µM. After seven rounds of MPPD with decreasing target concentration and increasing reference moiety concentration, 25.47% of the candidate nucleic acid agent immobilized particles showed binding to 100 pM HRP-2 in 10% serum (FIG. 5B).

B. Verification:

The verification results of the method according to the present disclosure of selected candidate nucleic acid agents for HRP-2 is illustrated in FIG. 6E: an HRP-2 candidate nucleic acid agent with a $K_D$ of 0.13 nM in buffer and 0.12 nM in serum. In another word, the most abundant candidate nucleic acid agent (HRP-2-702) from this pool showed high affinity and specificity for HRP-2, with a $K_D$ of 128 pM in buffer that was essentially unchanged (124 pM) in 10% serum.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for identifying one or more nucleic acid agents having a desired property from a mixture of candidate nucleic acid agents, said desired property is specific binding to a target with high affinity, wherein the mixture of candidate nucleic acid agents comprises a plurality of aptamers, the method comprising:

providing a plurality of particles with the candidate nucleic acid agents immobilized thereon, wherein each of the plurality of particles comprises at most a subset of the candidate nucleic acid agents within said mixture;

exposing the plurality of particles to a screening composition comprising a target moiety and a reference moiety, wherein an interaction of said candidate nucleic acid agents with the target moiety is indicated by a first signal, an interaction of said candidate nucleic acid agents with the reference moiety is indicated by a second signal, and an intensity of said first signal together with an intensity of said second signal for a particular particle provide a sorting parameter of the particular particle, wherein a concentration of the target moiety and a concentration of the reference moiety are respectively set at a value enabling the sorting parameter of about 0.05% to about 1% of the plurality of particles to be within a predetermined sorting range, wherein the reference moiety is a protein or a polypeptide moiety;

isolating from said plurality of particles one or more selected particles having a sorting parameter within said predetermined sorting range, wherein the one or more selected particles comprises said one or more nucleic acid agents having the desired property; and identifying the one or more nucleic acid agents having the desired property from the one or more selected particles.

2. The method according to claim 1, wherein said sorting range is determined with a first threshold and a second threshold, and the sorting parameter of a particular particle is within said sorting range when the intensity of the first signal of the particular particle is above said first threshold and the intensity of the second signal of the particular particle is below said second threshold.

3. The method according to claim 2, wherein said first threshold is determined by a process comprising:

exposing the plurality of particles with the mixture of candidate nucleic acid agents immobilized thereon to a first prescreening composition comprising a saturating concentration of the target moiety, and determining a maximum mean intensity of a signal indicating an interaction of said candidate nucleic acid agents with the target moiety in said first prescreening composition, wherein said first prescreening composition does not comprise the reference moiety.

4. The method according to claim 3, wherein said first threshold is set to be at least one half of said maximum mean intensity of the signal indicating an interaction of said candidate nucleic acid agents with the target moiety in said first prescreening composition.

5. The method according to claim 2, wherein said second threshold is determined by a process comprising:

exposing the plurality of particles with the mixture of candidate nucleic acid agents immobilized thereon to a second prescreening composition comprising a saturating concentration of the reference moiety, and determining a maximum mean intensity of a signal indicating an interaction of said candidate nucleic acid agents with the reference moiety in said second prescreening composition, wherein said second prescreening composition does not comprise the target moiety.

6. The method according to claim 5, wherein said second threshold is set to be at most one tenth of the maximum mean intensity of the signal indicating an interaction of said candidate nucleic acid agents with the reference moiety in said second prescreening composition.

7. The method according to claim 1, wherein a ratio between the concentration of the target moiety and the concentration of the reference moiety in the screening composition is from about $1:10^9$ to about 1:1.

8. The method according to claim 1, wherein the target moiety is a protein or a polypeptide moiety.

9. The method according to claim 1, wherein the reference moiety comprises serum proteins.

10. The method according to claim 1, further comprising c2) generating an enriched mixture of candidate nucleic acid agents from the selected particle prior to the operation d).

11. The method according to claim 10, wherein operations a), b), c), and c2) constitute one round of screening, and the method comprises two or more said rounds of screening, wherein the enriched mixture of candidate nucleic acid agents obtained from operation c2) of one round of screening is used as the mixture of candidate nucleic acid agents to be immobilized onto the plurality of particles in operation a) of the next round of screening.

12. The method according to claim 1, wherein the target moiety comprises a protein or a part thereof selected from the group consisting of Tumor Necrosis Factor α, Neutrophil Gelatinase-Associated Lipocalin, Histidine-Rich Protein 2, Platelet-Derived Growth Factors, Vascular Endothelial Growth Factors, Angiopoietins, Complement proteins and Integrins.

* * * * *

```
                             SEQUENCE LISTING

<160> NUMBER OF SEQ ID NOS: 8

<210> SEQ ID NO 1
<211> LENGTH: 81
<212> TYPE: DNA
<213> ORGANISM: Artificial Sequence
<220> FEATURE:
<223> OTHER INFORMATION: S01, TNF-&A in serum

<400> SEQUENCE: 1
atccagagtg acgcagcatg cttaaggggg gggcgggtta agggagtggg gagggagctg      60
gtgtggacac ggtggcttag t                                                81

<210> SEQ ID NO 2
<211> LENGTH: 80
<212> TYPE: DNA
<213> ORGANISM: Artificial Sequence
<220> FEATURE:
<223> OTHER INFORMATION: B01, TNF-&A in buffer

<400> SEQUENCE: 2
atccagagtg acgcagcagg ttaaggtgta ggtccgggtg gggggtggg ttgggggact       60 ggtggacacg gtggcttagt                                                  80

<210> SEQ ID NO 3
<211> LENGTH: 80
<212> TYPE: DNA
<213> ORGANISM: Artificial Sequence
<220> FEATURE:
<223> OTHER INFORMATION: NGAL-05, NGAL in serum

<400> SEQUENCE: 3
gaattccgcc ctcgtcccat ctcggcttgg tatggcggag ctggatagta tagtcggaac      60
accaaccgag aacggaattc                                                  80

<210> SEQ ID NO 4
<211> LENGTH: 80
<212> TYPE: DNA
<213> ORGANISM: Artificial Sequence
<220> FEATURE:
<223> OTHER INFORMATION: HRP-2-702, HRP-2 in serum

<400> SEQUENCE: 4
atccagagtg acgcagcatt aaatagggt ttggctttgg gtctggcata taggaacaag       60
tttggacacg gtggcttagt                                                  80

<210> SEQ ID NO 5
<211> LENGTH: 80
<212> TYPE: DNA
```

```
<213> ORGANISM: Artificial Sequence
<220> FEATURE:
<223> OTHER INFORMATION: 18nt PCR primer sites
<220> FEATURE:
<221> NAME/KEY: misc_feature
<222> LOCATION: (19)..(62)
<223> OTHER INFORMATION: n is a, c, g, or t

<400> SEQUENCE: 5
atccagagtg acgcagcann nnnnnnnnnn nnnnnnnnnn nnnnnnnnnn nnnnnnnnnn     60
nntggacacg gtggcttagt                                                 80

<210> SEQ ID NO 6
<211> LENGTH: 80
<212> TYPE: DNA
<213> ORGANISM: Artificial Sequence
<220> FEATURE:
<223> OTHER INFORMATION: 23-nt PCR primer sites
<220> FEATURE:
<221> NAME/KEY: misc_feature
<222> LOCATION: (24)..(57)
<223> OTHER INFORMATION: n is a, c, g, or t

<400> SEQUENCE: 6
gaattccgcc ctcgtcccat ctcnnnnnnn nnnnnnnnnn nnnnnnnnnn nnnnnnnaac     60
accaaccgag aacggaattc                                                 80

<210> SEQ ID NO 7
<211> LENGTH: 18
<212> TYPE: DNA
<213> ORGANISM: Artificial Sequence
<220> FEATURE:
<223> OTHER INFORMATION: 5'-amino-modified FP
<220> FEATURE:
<221> NAME/KEY: misc_feature
<222> LOCATION: before (1)
<223> OTHER INFORMATION: PEG18

<400> SEQUENCE: 7
atccagagtg acgcagca                                                   18

<210> SEQ ID NO 8
<211> LENGTH: 23
<212> TYPE: DNA
<213> ORGANISM: Artificial Sequence
<220> FEATURE:
<223> OTHER INFORMATION: 5'-amino-modified FP
<220> FEATURE:
<221> NAME/KEY: misc_feature
<222> LOCATION: before (1)
<223> OTHER INFORMATION: PEG18

<400> SEQUENCE: 8
gaattccgcc ctcgtcccat ctc                                             23
```